United States Patent
Cordisco

(10) Patent No.: US 9,452,021 B2
(45) Date of Patent: Sep. 27, 2016

(54) SYSTEMS, METHODS, AND APPARATUS FOR RESUSPENDING CELLS FROM SURGICAL LAUNDRY

(71) Applicant: Michael Christopher Cordisco, Brookfield, CT (US)

(72) Inventor: Michael Christopher Cordisco, Brookfield, CT (US)

(73) Assignee: All Cell Recovery LLC, Brookfield, CT (US)

(*) Notice: Subject to any disclaimer, the term of this patent is extended or adjusted under 35 U.S.C. 154(b) by 52 days.

(21) Appl. No.: 14/060,663

(22) Filed: Oct. 23, 2013

(65) Prior Publication Data

US 2015/0037305 A1    Feb. 5, 2015

Related U.S. Application Data

(60) Provisional application No. 61/861,953, filed on Aug. 2, 2013.

(51) Int. Cl.
| | | |
|---|---|---|
| A61M 1/02 | (2006.01) | |
| A61B 19/00 | (2006.01) | |
| B01F 11/00 | (2006.01) | |

(52) U.S. Cl.
CPC ............ *A61B 19/34* (2013.01); *A61M 1/0272* (2013.01); *B01F 11/0002* (2013.01); *B01F 11/0088* (2013.01)

(58) Field of Classification Search
CPC  A61B 19/34; A61M 1/0272; A61M 1/0281; B01F 11/0002; B01F 11/0088
See application file for complete search history.

(56) References Cited

U.S. PATENT DOCUMENTS

| | | |
|---|---|---|
| 1,886,578 A | 11/1932 | Pedrazzo |
| 2,516,655 A * | 7/1950 | Smith .............................. 68/174 |
| 2,804,075 A | 8/1957 | Borden |
| 3,896,733 A | 7/1975 | Rosenberg |
| 3,965,896 A | 6/1976 | Swank |
| 3,971,381 A | 7/1976 | Gibson |
| 4,014,329 A | 3/1977 | Welch et al. |
| 4,098,728 A | 7/1978 | Rosenblatt |
| 4,157,965 A | 6/1979 | Raible |
| 4,205,680 A | 6/1980 | Marshall |
| 4,389,207 A | 6/1983 | Bacehowski et al. |
| 4,626,251 A | 12/1986 | Shen |
| 4,642,088 A | 2/1987 | Gunter |
| 4,650,481 A | 3/1987 | O'Connor et al. |
| 4,657,529 A | 4/1987 | Prince et al. |
| 4,886,487 A | 12/1989 | Solem et al. |
| 4,976,682 A | 12/1990 | Lane et al. |
| 5,055,198 A | 10/1991 | Shettigar |
| 5,153,131 A | 10/1992 | Wolf et al. |
| 5,234,608 A | 8/1993 | Duff |
| 5,242,384 A | 9/1993 | Robinson |
| 5,378,227 A | 1/1995 | O'Riordan et al. |
| 5,407,425 A | 4/1995 | Werner et al. |
| 5,417,649 A | 5/1995 | Kawahara et al. |
| 5,563,584 A | 10/1996 | Rader et al. |
| 5,681,709 A | 10/1997 | Mochnal |
| 5,707,517 A * | 1/1998 | Rolchigo et al. ............. 210/232 |
| 5,814,550 A | 9/1998 | Wolcott |
| 5,876,611 A | 3/1999 | Shettigar |
| 5,923,001 A | 7/1999 | Morris et al. |
| 5,971,948 A | 10/1999 | Pages et al. |
| 5,976,388 A | 11/1999 | Carson |
| 6,059,968 A | 5/2000 | Wolf |
| 6,197,207 B1 | 3/2001 | Chapman et al. |
| 6,241,947 B1 | 6/2001 | Komatsu et al. |
| 6,251,295 B1 | 6/2001 | Johnson |
| 6,329,438 B1 | 12/2001 | Cercone et al. |
| 6,558,341 B1 | 5/2003 | Swisher |
| 6,814,862 B2 | 11/2004 | Biesel |
| 6,910,488 B2 | 6/2005 | McConnell et al. |
| 6,942,633 B2 | 9/2005 | Odland |
| 7,641,794 B2 | 1/2010 | Oka et al. |
| 7,695,627 B2 | 4/2010 | Bosch et al. |
| 7,713,227 B2 | 5/2010 | Wholey et al. |
| 7,776,263 B2 | 8/2010 | East |
| 8,409,125 B2 | 4/2013 | Bobroff |
| 8,414,519 B2 | 4/2013 | Hudspeth et al. |
| 2006/0108288 A1 | 5/2006 | Oishi |
| 2008/0058695 A1 | 3/2008 | Perovitch et al. |
| 2009/0314724 A1 | 12/2009 | Nierich |
| 2012/0165642 A1 | 6/2012 | Krensky et al. |
| 2014/0047986 A1 | 2/2014 | Robinson |
| 2014/0050615 A1 | 2/2014 | Robinson |

FOREIGN PATENT DOCUMENTS

| | | |
|---|---|---|
| EP | 0312507 | 4/1989 |
| EP | 0957155 | 1/2000 |
| EP | 2059161 | 12/2012 |

OTHER PUBLICATIONS

International Search Report for PCT/US2014/049461 dated Feb. 9, 2015; 4 pps.
Written Opinion for PCT/US2014/049461 dated Feb. 9, 2015; 8 pps.
Ronai et al., "Improving Autologus Blood Harvest: Recovery of Red Blood Cells from Sponges and Suction" Anesthesia and Intensive Care; Nov. 1987; vol. 15(4), 421-424; 4 pages.
Waters, Jonathan, "Intraoperative Blood Conservation—Every Cell is Sacred", International Trauma Anesthesia and Critical Care society, Summer 2005, 5 pages.

(Continued)

*Primary Examiner* — Kara Johnson

(74) *Attorney, Agent, or Firm* — Michael D. Downs; Fincham Downs LLC

(57) ABSTRACT

Systems, apparatus, methods, and articles of manufacture provide for resuspending and/or collecting blood or other types of cells from used surgical sponges and/or other types of surgical articles.

22 Claims, 14 Drawing Sheets

(56) References Cited

OTHER PUBLICATIONS

Takaori, Masuhiko, "Perioperative autotransfusion: haemodilution and Red Cell Salvaging" Canadian Journal of Anesthesia; 604-607; 4 pages, 1991.

Haynes, S.L. et al., "Does washing swabs increase the efficiency of red cell recovery by cell salvage in aortic surgery?" Vox Sanguinis, May 2005, vol. 88, Issue 4, 244-248; 5 pages.

Horvath, Keith, et al., "Blood Transfusion and Infection after Cardiac Surgery" Annals of Thoracic Surgery, 2013; 95:2194-201; 8 pages.

Ruyin Jin, et al., "Effect of Hospital Culture on Blood Transfusion in Cardiac Procedures" Annals of Thoracic Surgery, 2013; 95:1269-75; 7 pages.

Peasah, Samuel et al., "Medicare Non Payment of Hospital Acquired Infections: Infection Rates Three Years Post Implementation" Medicare and Medicaid Research Review; 2013: vol. 3, No. 3; 16 pages.

"Swab Washing", UK Cell Salvage Action Group—ICS Technical Factsheet; Version 2; 2 pages, Jul. 2013.

* cited by examiner

US 9,452,021 B2

SYSTEMS, METHODS, AND APPARATUS FOR RESUSPENDING CELLS FROM SURGICAL LAUNDRY

CROSS-REFERENCE TO RELATED APPLICATIONS

The present application claims the benefit of priority of U.S. Provisional Patent Application No. 61/861,953 filed Aug. 2, 2013, entitled "SPONGE WASHING SYSTEM," which is incorporated by reference in the present application.

BRIEF DESCRIPTION OF THE DRAWINGS

An understanding of embodiments described in this disclosure and many of the related advantages may be readily obtained by reference to the following detailed description when considered with the accompanying drawings, of which.

DETAILED DESCRIPTION

A. Introduction

Figure 1:
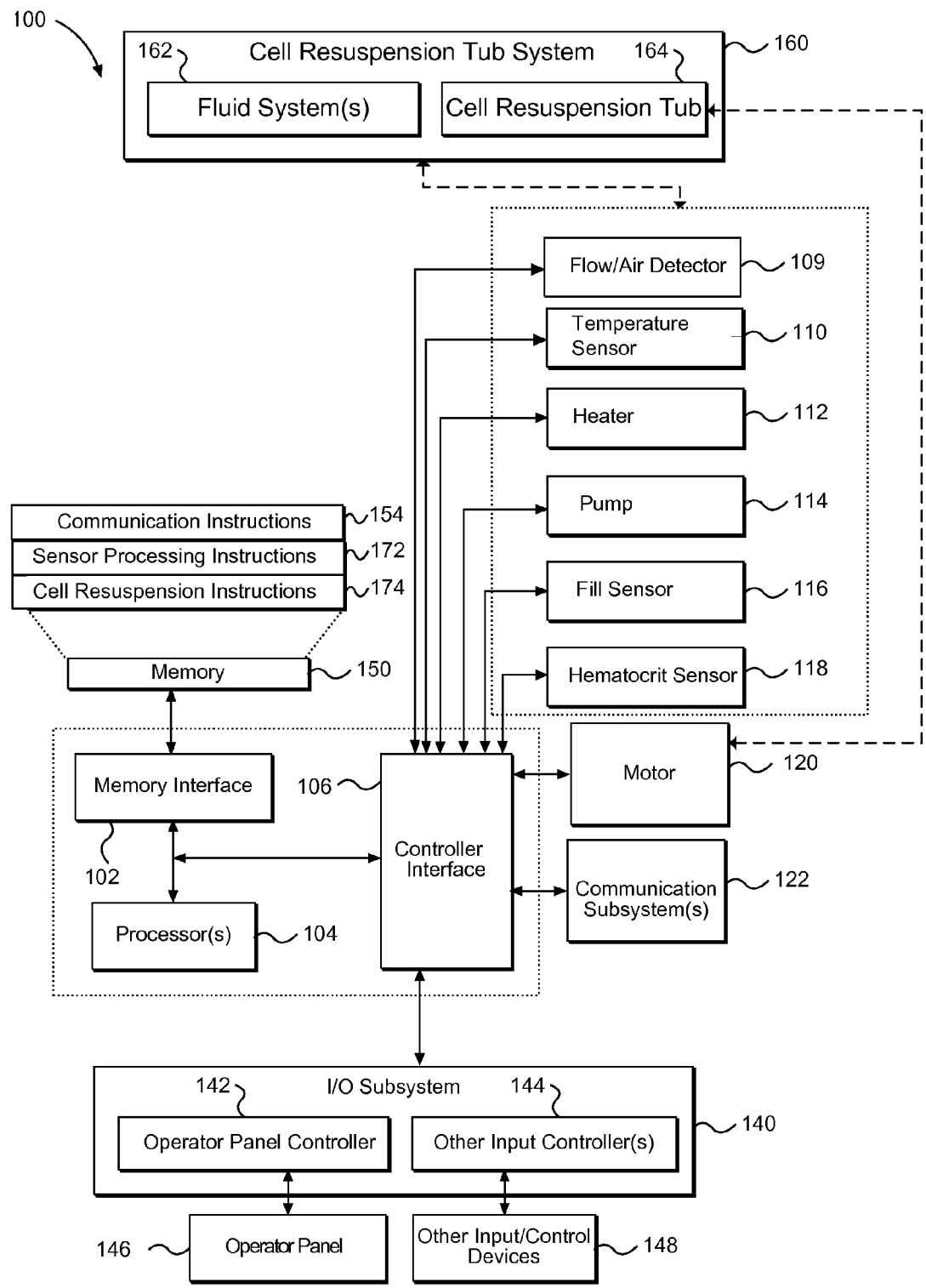
FIG. 1 is a block diagram of a cell resuspension system according to one or more embodiments.

Applicants have recognized that, in accordance with some embodiments described in this disclosure, some types of medical professionals and other types of users (e.g., auto-transfusion specialists, nurses, perfusionists, surgeons, and other types of medical professionals) may find it beneficial to reclaim, recover, and/or resuspend blood and other types of body cells of a patient from various types of surgical articles. In one embodiment, resuspended blood may be stored for re-infusion and/or re-infused to a patient (e.g., during a current medical procedure).

Applicants have further recognized that, in accordance with some embodiments described in this disclosure, rinsing and/or soaking surgical sponges and other types of surgical laundry with physiologic suspension solution may dilute coagulation components of whole blood, thereby making clotting of the blood in the laundry and/or in a cell saver less likely, yielding more salvageable blood from the laundry. Applicants have further recognized that, in accordance with some embodiments described in this disclosure, by rinsing and/or soaking surgical laundry the laundry may become saturated with suspension fluid, further liberating blood (e.g., from woven cotton fibers). Applicants have further recognized that, in accordance with some embodiments described in this disclosure, one or more types of medications, surfactants, antibiotics, and/or other agents (e.g., anticoagulant citrate phosphate dextrose (CPD) solution, heparin, albumin) may be added directly to soaking tub or to a physiologic solution to increase the yield of blood retrieved from surgical articles and/or to increase the viability of recovered blood.

Applicants have further recognized that, in accordance with some embodiments described in this disclosure, in may be advantageous to provide for a cell reclamation system, method, and apparatus providing for and/or utilizing one or more of: normothermic blood (e.g., at 98.6 F and/or allowing for normal oxygen unloading); automation of one or more steps of cell reclamation; increased viability of recovered blood by dilution of the blood in a suspension fluid; improved determination and monitoring of an indication of a volume of blood lost to sponges and other surgical laundry; determining and storing an indication of the number of cycles undertaken in a cell reclamation process; a cell reclamation apparatus that is closed to the environment and/or reduces risks of splatter and/or airborne contamination; and/or automatically sending blood-laden suspension fluid to a cell saver without disruption of any ongoing cell saver field collection.

In accordance with one or more embodiments of the present invention, systems, methods, apparatus, and articles of manufacture are described that provide for one or more of the following functions: liberating, reclaiming, releasing, retrieving, extracting, recovering, resuspending, and/or collecting blood or other types of cells from used surgical sponges and/or other types of surgical articles (e.g., that absorbed, came into contact with, received, and/or were used to collect or clean up blood during a surgical procedure); warming physiologic fluid to a desired temperature or temperature range (e.g., a normothermic temperature); transmitting physiologic fluid to a tub or other vessel for use in extracting (e.g., by soaking and/or agitating) cells from surgical articles (e.g., surgical sponges placed in a vessel by an operator at a surgical field); adding one or more types of agents to a physiologic fluid (e.g., for increasing the yield and/or viability of recovered cells); soaking one or more surgical articles in a physiologic solution; suspending recovered blood in a physiologic suspension solution; and/or preparing recovered blood for re-infusion to a patient (e.g., using a cell saver or other type of autologous cell salvage device).

In accordance with one or more embodiments of the present invention, systems, methods, apparatus, and articles of manufacture are described that provide for an automated device configured to extract blood from surgical sponges and to re-suspend that blood at an approximately normothermic temperature in a physiologic solution for processing by an autotransfusion device (e.g., a cell saver). In some embodiments, a device is configured to liberate blood from bloody surgical sponges and prepare the reclaimed blood for processing (e.g., by an autologous cell salvage device) for re-infusion to a patient. In one embodiment, the device warms a physiologic fluid to a normothermic temperature (and/or receives a warmed physiologic fluid), transmits the warmed physiologic fluid to a vessel for soaking surgical sponges used to collect blood, and, in accordance with an automated process, recovers and resuspends the blood form the surgical sponges into a physiologic suspension solution.

In accordance with one or more embodiments of the present invention, systems, methods, apparatus, and articles of manufacture are described that provide for a reusable agitator device and a disposable, single-use tub system, including a soaking tub and a tubing set, for use with the reusable agitator device.

B. Definitions

The terms "cell resuspension tub" and "soaking tub" may be used synonymously in this application to refer to a tub, drum, or other type of vessel used for holding surgical articles (e.g., surgical laundry) and/or fluid (e.g., for resuspending cells from the surgical laundry in a fluid solution). In accordance with some embodiments, a cell resuspension tub may be spun, rotated, vibrated, shaken, and/or otherwise agitated. In some embodiments, a cell resuspension tub may refer to a vessel comprising, connected to, and/or coupled with one or more components such as, without limitation, one or more fins, sensors, heaters, and/or connectors (e.g., for coupling the vessel to a motor or other agitator device).

The term "cell resuspension tub system" may be used in this application to refer to a cell resuspension tub and one or more other types of components with which the cell resuspension tub may be connected, coupled, manufactured, packaged, marketed, and/or sold (e.g., as a sterile kit). In some embodiments, a cell suspension tub and/or one or more other components may be sterile, disposable, and/or intended for only one use. Components of a cell resuspension tub system may comprise, by way of example and not limitation, one or more of: tubing, fluid, a pump, a sensor, and/or a heater, etc. In accordance with some embodiments, a sterile, single-use, disposable cell resuspension tub system comprising a soaking tub, inlet tubing for filling the soaking tub with fluid, and outlet tubing for emptying the soaking tub, may be referred to as a "tub kit."

The terms "cell resuspension agitator device" and "agitator device" may be used synonymously in this application to refer to any electro-mechanical device configured to agitate a cell suspension tub (e.g., to assist in forcing and/or drawing out cells captured in surgical laundry and into a suspending solution). In some embodiments, a cell resuspension agitator device may comprise a motor configured to be coupled to a soaking tub. In some embodiments, a cell resuspension agitator device may comprise means for agitating a soaking tub and one or other components (e.g., sensors, displays, etc.) and/or controllers for controlling one or more functions of a cell resuspension process. In one or more embodiments, a cell resuspension agitator device may be embodied as and/or embodied in an integrated cell resuspension appliance that also includes software and/or hardware controllers for various aspects of a cell resuspension process.

The terms "cell resuspension controller device" and "controller device" may be used synonymously in this application to refer to any electro-mechanical device configured for controlling one or more functions of a cell resuspension process (e.g., filling a tub and/or emptying a tub; pumping, heating, monitoring, sensing, and/or measuring fluid, etc.). In one example, a controller device may comprise a computing device (e.g., a personal computer, a table computer) connected to an agitator device for controlling agitation of a soaking tub and to a fluid intake/output system for controlling the filling and emptying of the soaking tub. In one or more embodiments, a cell resuspension controller device may be embodied as and/or embodied as a single unit or appliance as an integrated cell resuspension appliance configured to receive one or more components (e.g., tubing) of a cell resuspension tub system and also including an agitator device for agitating a cell resuspension tub when the tub is connected to the integrated cell resuspension appliance.

The term "cell resuspension system" may be used in this application to refer to any combination of two or more of: a cell resuspension tub, a cell resuspension tub system, a fluid system (e.g., tubing, fluid, and/or a pump), a sensor, an agitator device, a controller device, an integrated cell resuspension appliance, and/or a cell saver. In one example, a cell resuspension system may comprise a soaking tub coupled to a motor. In one or more embodiments, a cell resuspension system may comprise a cell resuspension tub system and an integrated cell resuspension appliance. In some embodiments, a cell resuspension system may comprise a sterile, disposable tub kit including a soaking tub and intake and/or output fluid systems, and a reusable, integrated cell resuspension appliance (e.g., to which the soaking tub and fluid system(s) are connected for resuspending cells from surgical laundry).

The term "surgical sponge" may be used in this application to refer to a type of surgical laundry typically made of a woven cotton or other mesh material and designed to capture fluids (e.g., blood) that may leak from a body (e.g., during a surgical procedure). Some examples of surgical sponges include, without limitation, laparotomy sponges, lap pads, gauze pads, swabs, and X-ray detectable sponges.

C. General Systems and Structures

FIG. 1 depicts a block diagram of an example architecture for a cell resuspension system 100 for facilitating the resuspension of cells from surgical laundry and other articles, according to one or more embodiments. The cell resuspension system 100 may include a memory interface 102, one or more data processors, image processors, and/or central processing units 104, and a controller interface 106. The memory interface 102, the one or more processors 104, and/or the controller interface 106 may be separate components or may be integrated in one or more integrated circuits. The various components in the cell resuspension system 100 may be coupled by one or more communication buses or signal lines.

Sensors, devices, and subsystems may be coupled to the controller interface 106 to facilitate multiple functionalities. For example, a flow/air detector 109, a temperature sensor 110, a heater 112, a pump 114, a fill sensor 116, a hematocrit sensor 118, and a motor 120 may be coupled to the controller interface 106 to facilitate heating, filling, monitoring, suspending, and/or draining functions described in this disclosure with respect to various embodiments.

In some embodiments, as discussed in this disclosure, the motor 120 may be configured (e.g., via a drive shaft and/or connector) to agitate a cell resuspension tub containing fluid and surgical laundry and/or other surgical articles (not shown), and the motor 122 (which may be embodied as an agitator device) may receive controlling signals via the controller interface 106. As discussed in this disclosure, one or more temperature sensors 110, heaters 112, and/or hematocrit sensors 118 may, in accordance with some embodiments, be embodied in one or more of a cell resuspension tub, agitator device, and/or tubing system (not shown) of a cell resuspension system 100. In one example, based on a reading received from a temperature sensor 110, the processor(s) 104 may direct a heater 112 to turn on or off, or to otherwise provide or cease providing heat (e.g., to fluid in a tubing system). As also discussed in this disclosure, one or more pumps 114 may, in accordance with some embodiments, be embodied in one or more of a cell resuspension tub system and/or tubing system of a cell resuspension system 100 (e.g., for controlling the transmission of fluid into and/or out of a cell resuspension tub). In one example, based on a signal from a fill sensor 116 indicating that a cell resuspension tub has reached a predetermined level, the processor(s) 104 may direct a pump 114 to stop pumping fluid and/or may direct a motor 120 to turn on and/or engage a drive shaft to rotate or otherwise agitate the cell resuspension tub.

According to some embodiments, communication functions of a cell resuspension system may be facilitated through one or more wired and/or wireless communication subsystem(s) 122. According to some embodiments, cell resuspension information and/or patient information may be received from and/or transmitted to the processor(s) 104 via communication subsystem(s) 122. Communications may, in one or more embodiments, be associated with a "network" or a "communication network". As used in this disclosure, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. In some embodiments, networks may be hard-wired, wireless, virtual, neural, and/or any other configuration or type of network that is or becomes known. Networks may comprise any number of computers and/or other types of devices in communication with one another, directly or indirectly, via a wired or wireless medium such as the Internet, LAN, WAN or Ethernet (or IEEE 802.3), Token Ring, RF, cable TV, satellite links, or via any appropriate communications means or combination of communications means. In some embodiments, a network may include one or more wired and/or wireless networks operated in accordance with any communication standard or protocol that is or becomes known or practicable. Exemplary protocols for network communications include but are not limited to: the Fast Ethernet LAN transmission standard 802.3-2002® published by the Institute of Electrical and Electronics Engineers (IEEE), Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Communication between and/or among devices may be encrypted to ensure privacy and/or prevent fraud in any one or more of a variety of ways well known in the art. The specific design and embodiment of the communication subsystem 122 may depend on the communication network(s) over which the cell resuspension system 100 is intended to operate for a desired implementation.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

The I/O subsystem 140 may include operator panel controller 142 and/or other input controller(s) 144. The operator panel controller 142 may be coupled, for example, to an operator panel 146 (e.g., a touch screen, a button panel). The operator panel 146 and operator panel controller 142 may, for example, detect the actuation by a user of one or more hardware buttons and/or switches. A touch screen may, for example, also be used to implement virtual or soft buttons and/or a keyboard. For example, the operator panel 146 and operator panel controller 142 may, in a touch screen embodiment, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the operator panel 146. The user may be able, in some embodiments, to customize a functionality of one or more buttons or other input means of the operator panel 146.

The other input controller(s) 144 may be coupled to other input/control devices 148, such as one or more buttons, rocker switches, thumb-wheel, infrared port, USB port, and/or a pointer device such as a mouse or stylus.

The memory interface 102 may be coupled to memory 150. The memory 150 may include high-speed random access memory and/or non-volatile memory, such as one or more magnetic disk storage devices, one or more optical storage devices, and/or flash memory (e.g., NAND, NOR). The memory 150 may store an operating system (not system), such as ANDROID, DARWIN, RTXC, LINUX, UNIX, OS X, WINDOWS.

The memory 150 may also store communication instructions 154 to facilitate communicating with one or more additional devices, one or more computers and/or one or more servers.

The memory 150 may include sensor processing instructions 172 to facilitate sensor-related processing and functions and/or cell resuspension software instructions 174 to facilitate any one or more of various other processes and functions for resuspending cells, a described in this disclosure.

Each of the above identified instructions and applications may correspond to a set of instructions for performing one or more functions described above. These instructions need not be implemented as separate software programs, procedures, or modules. The memory 150 may include additional instructions or fewer instructions. Furthermore, various functions of the cell resuspension system 100 may be implemented in hardware and/or in software, including in one or more signal processing and/or application specific integrated circuits.

As depicted in FIG. 1, cell resuspension system 100 may comprise a cell resuspension tub system 160, as discussed with respect to various embodiments in this disclosure. Cell resuspension tub system 160 may comprise one or more fluid systems 162 (e.g., an inlet tubing system, an output tubing system) and one or more cell resuspension tubs 164. Various examples of fluid systems and cell resuspension tubs are discussed in this disclosure. As indicated in FIG. 1, in accordance with some embodiments, cell resuspension tub 164 may be configured for connecting with motor 120 and/or may be mechanically coupled to motor 120. As depicted in FIG. 1, in some embodiments, one or more components of cell resuspension tub system 160 (e.g., inlet tubing, cell resuspension tub 164) may be connected to, may comprise, and/or may be configured to be received by one or more of the components in communication with the controller interface 106. In one example, cell resuspension tub 164 may comprise one or more fill sensors 116 configured to communicate with the processor(s) 104 via controller interface 106 (e.g., for indicating when the cell resuspension tub 164 has been filled with fluid to a predetermined level). In another example, a portion of inlet tubing of a fluid system 164 may be loaded through a heater 112.

Figure 2:
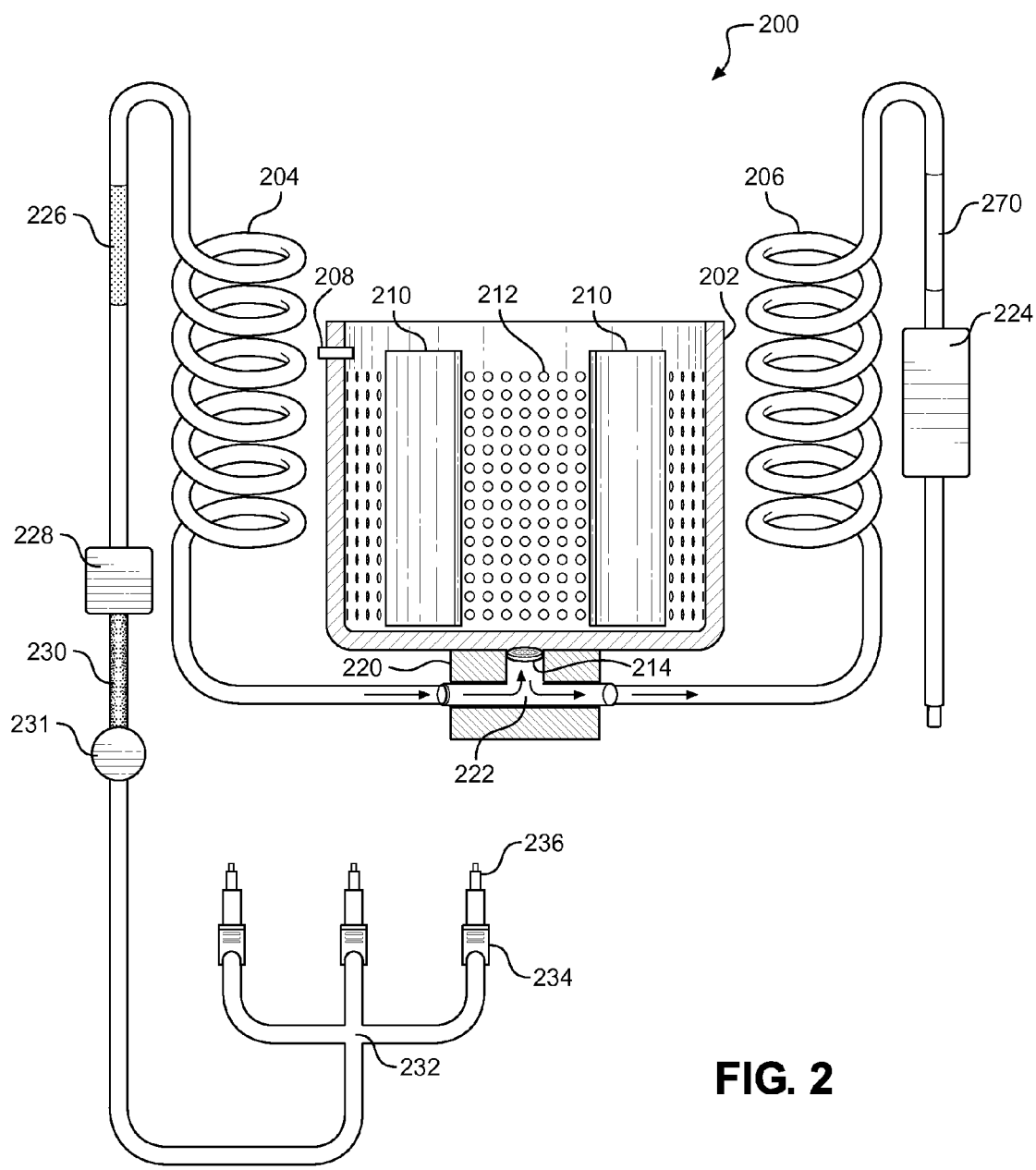
FIG. 2 is a cross-section view of a cell resuspension tub system according to one or more embodiments.

FIG. 2 depicts a cross-section view of an example cell resuspension tub system 200 according to one or more embodiments. According to some embodiments, cell resuspension tub system 200 may comprise one or more of the following components: a tub, a fin, a sensor (e.g., a fill sensor, a hematocrit sensor), a tub wall opening, a filter, a connector, a heat exchange element, tubing, a compressible segment, a tubing guide, a tubing connection, a clamp, an intravenous (IV) bag spike, and/or an IV bag.

According to some embodiments, soaking tub 202 comprises a vessel or container with an opening at one end for receiving (e.g., from a user) one or more articles (e.g., surgical sponges and/or other types of surgical laundry) that include cells (e.g., blood cells) and/or fluids (e.g., blood). In one example, a user may place surgical sponges that include blood and/or other bodily fluids collected during a surgical or other medical procedure (e.g., sponges that have been used to soak up or otherwise retain surgical blood) into the soaking tub 202. According to some embodiments, soaking tub 202 is configured to be mounted in, on, or otherwise connected mechanically to an agitator device and/or a cell resuspension controller device. According to some embodiments, soaking tub 202 comprises a sterile tub or drum for only a single use.

According to some embodiments, soaking tub 202 comprises an open-ended container or drum of metal or other rigid material. In one example, soaking tub 202 comprises a "U"-shaped vessel.

According to some embodiments, the soaking tub 202 may have an inner diameter in the range of 15-21 inches (e.g., 18 inches) and/or a height in the range of 12-18 inches (e.g., 15 inches). In one example embodiment, soaking tub 202 may have a volume capacity suitable for filling with approximately 2684 ml of physiologic fluid (e.g., in addition to one or more articles for soaking). It will readily understood that any particular dimensions of the soaking tub may be used as deemed desirable for a particular implementation (e.g., for particular types and/or sizes of surgical articles).

In one or more embodiments, one or more inner and/or outer surfaces of the soaking tub 202 may comprise an anti-thrombotic surface, bio-passive surface, and/or a bio-compatible surface configured to interact with blood for the purposes of reducing the inflammatory process or eliminating the possibility of thrombus formation and/or platelet adhesion. In some embodiments, a surface may be prepared by applying or coating the surface with an anti-thrombotic substance (e.g., X coating by Terumo, Inc.).

In some embodiments, soaking tub 202 comprises dual walls, such as an inner tub wall and an outer tub wall. In one embodiment, an innermost (medial) wall of the soaking tub 202 is circumferentially perforated with one or more openings 212. Accordingly, the inner tub wall may, in some embodiments, allow fluid and/or recovered cells to pass through the fenestrated wall via the openings 212, while retaining any surgical laundry or other articles within the inner tub wall (e.g., when the tub is drained via the outlet tubing).

According to one example, openings 212 comprise, by way of example and without limitation, round holes ½ of an inch in diameter and approximately ½ of an inch apart from one another. It will readily understood that any number of holes and/or any one or more diameters may be used as deemed desirable for a particular implementation (e.g., for particular types and/or sizes of surgical articles). In one embodiment, openings 212 extend from the bottom of the soaking tub 202 up to within 3 inches from the top the soaking tub. For example, there may be no openings in the top one to two inches of soaking tub 202.

According to some embodiments, one or more blades or fins 210 may be connected to one or more of the interior bottom and/or inner wall of the soaking tub 202. When the soaking tub 202 is rotated (e.g., by a motor), the fins 210 may assist in agitating any fluid in the soaking tub 202, thereby acting on the fluid and/or surgical laundry in the tub to assist in liberating any cells collected in the surgical laundry. In one example, three uniform individual plastic "fins" project inward from the innermost (medial) wall of the soaking tub 202. In another example, each fin 210 measures 10-15 inches (e.g., 13 inches) from the bottom of the soaking tub 202 towards the top and extending in toward the middle of the tub 2¾ inches. In one embodiment, the shape of a fin may be configured to facilitate removal of surgical laundry by hand. In one example, the fins may be tapered, rounded, or otherwise shaped and/or sized in order to accommodate the introduction of a user's hand into the interior of the soaking tub 202 (e.g., without edges or protrusions that may cut or pierce a user's skin and/or gloves).

According to some embodiments, one or more of the fins 210 may comprise fenestrations, gaps, passages, or other types of openings in the structure of the fin allowing at least some fluid in the soaking tub 202 to pass through the fin (e.g., as the fin is agitating the fluid). Applicant has recognized that allowing for fluid to pass through a fin may beneficially eliminate splashing of the fluid and/or may preserve some of the rotational energy of the suspension fluid as it is rotating, which may more improve the efficiency of reclaiming cells from surgical laundry. In an embodiment without such fenestrations, the potential motion of the fluid is more limited (e.g., to movement between or around two adjacent fins).

In one or more embodiments, the soaking tub 202 may comprise at least one fill sensor 208 for detecting at least one of: presence of a predetermined level of fluid in the soaking tub 202 and/or a volume of fluid in the soaking tub 202. In one embodiment, fill sensor 208 comprises a sensor for detecting when a level of fluid reaches a predetermined height in the soaking tub 208. In one example, fill sensor 208 is inside the outermost wall of the soaking tub 202. Overfilling of the soaking tub may cause contamination (e.g., of the cell resuspension tub system, cell resuspension agitator device, and/or cell resuspension controller device) and/or loss of any bloody suspension fluid that spills out.

In one embodiment, fill sensor 208 may be configured so that when it comes into contact with fluid or otherwise detects the presence of fluid at a predetermined level of the soaking tub 208 (e.g., a maximum fill height), it sends a signal indicating it has detected fluid. In one or more embodiments the fill sensor 208 may comprise a sensor configured to detect a ground fault caused when some medium (e.g., fluid reaching a certain level in the soaking tub) creates an electrical connection between two points or nodes of the sensor.

For example, if soaking tub 202 is filled to the height of fill sensor 208, the sensor detects the presence of fluid and transmits a signal to a controller device. In one example, the controller device may terminate a fill process in response to receiving a signal from the fill sensor 208 (e.g., by stopping a roller pump or other type of pump device from pumping additional fluid into soaking tub 202). According to one embodiment, the fill sensor 208 is configured to prevent the overfilling of fluid by triggering the deactivating (e.g., by a controller device) of an inlet side occlusive roller pump from engaging.

In one embodiment, the fill sensor 208 comprises a sensor for determining a volume status of the soaking tub 202 in accordance with a volume equation:

$$V = h \times 3.14 \times r^2,$$

in which h and r represent the height and inner radius, respectively, of the soaking tub 202.

In one or more embodiments, soaking tub 202 and/or y-type tubing connection 222 may comprise one or more filters 214. Filter 214, in accordance with some embodiments, may be configured to prevent debris, clots, articles from which cells are being reclaimed, and/or other unwanted matter and materials, from exiting the soaking tub 202 and/or entering y-type tubing connection 222, inlet tubing 204, and/or outlet tubing 206. According to one or more embodiments, filter 214 is configured to allow resuspended cells (e.g., red blood cells) to pass out of the soaking tub 202, while retaining unwanted materials in the soaking tub 202.

In one example, red blood cells, suspended or otherwise carried along with physiologic fluid used to extract the red blood cells from bloody surgical articles, may pass through the filter at the bottom of soaking tub 202, into y-type tubing connection 222, and into outlet tubing 206, while the surgical articles remain in the soaking tub 202. According to some embodiments, filter 214 similarly may prevent (e.g., during a tub filling process) unwanted matter from entering soaking tub 214 via the inlet tubing 204 and/or y-type tubing connection 222.

In some embodiments, cell resuspension tub system 200 may comprise a connector for removably fixing, mounting, or otherwise connecting the soaking tub 202 to a drive source (e.g., a motor) for rotating the soaking tub 202. In one or more embodiments, a connector is attached to the underside of a soaking tub and is configured to be removably inserted or otherwise connected to a corresponding rotatable connector (e.g., a connecting end of a motor's drive shaft). When the connectors are connected and rotating, the soaking tub 202 is caused to rotate.

In some embodiments, a male connector 220 is attached to the underside of soaking tub 202 and is configured to be removably inserted or otherwise connected to a corresponding rotatable female connector (e.g., of an agitator device) for rotating the soaking tub 202. In one example, the male connector 220 comprises a multifaceted block of metal or other rigid material affixed to the soaking tub in a manner such that when the male connector 220 is rotated, it rotates the soaking tub 220. According to the example, the male connector is of a multifaceted shape designed to fit into a corresponding female connector for receiving and rotating the male connector 220.

Some examples of connector designs for removably securing and rotating the soaking tub 202 are discussed in this disclosure; various other ways of shaping and designing respective connectors to be rotatably connected to one another will be readily understood by those skilled in the art in light of the present disclosure.

According to some embodiments, male connector 220 comprises or may be coupled with y-type tubing connection 222. In one embodiment, male connector 220 may comprise: (i) one or more holes or channels allowing fluid to pass in and/or out of soaking tub 202 via y-type tubing connection 222, (ii) one or more holes or channels allowing fluid to pass into soaking tub 202 via inlet tubing 204, and/or (iii) one or more holes or channels allowing fluid to pass out of soaking tub 202 via outlet tubing 206.

According to some embodiments, inlet tubing 204 and/or outlet tubing 206 may comprise one or more coils. In some embodiments, coils of tubing 204 and/or 206 may be placed inside a controller device (e.g., an integrated cell resuspension appliance) with the soaking tub 202 and/or other components of a cell resuspension tub system 200.

Inlet tubing 204 and/or outlet tubing 206 may comprise polyvinyl chloride (PVC) tubing. In one or more embodiments, one or more inner and/or outer surfaces of the soaking tub 202 may comprise an anti-thrombotic surface, bio-passive surface, and/or a bio-compatible surface. In one embodiment, the inlet tubing 204 is 40 inches in length with a 3/16-inch inner diameter. In some embodiments, tubing may comprise one or more rigid plastic sleeves or other type of "tubing bend relief" for preventing kinking of the tubing. In various embodiments, tubing may comprise at least one sterile cap on an end of the tubing (e.g., to maintain sterility of the interior of the tubing prior to use).

In one embodiment, inlet tubing 204 may comprise at least one heat exchange segment 226 comprising a material suitable for conductive transfer of heat. For example, the heat exchange segment 226 may comprise stainless steel and/or other types of conductive metal. According to one example, the heat exchange segment 226 comprises stainless steel tubing (e.g., up to approximately 6 inches in length). In another example, the heat exchange segment 226 is not made of PVC or plastic. It will be readily understood that any length and/or material for a heat exchange element may be used as deemed desirable for a particular implementation.

In one or more embodiments, the location of the heat exchange segment 226 along inlet tubing 204 is configured to allow the heat exchange segment 226 to be inserted into or otherwise be in contact with a heating element and/or other heat exchange surface (e.g., integrated in a cell resuspension controller device and/or controlled by a cell resuspension controller device).

In one embodiment, inlet tubing 204, outlet tubing 206, and/or soaking tub 202 may comprise one or more heating elements for heating fluid(s).

According to some embodiments, inlet tubing 204 may comprise at least one compressible segment 230 comprising a material suited for mechanical compression and/or manipulation of the tubing segment. In one embodiment, compressible segment 230 comprises a compressible silastic material.

In one or more embodiments, compressible segment 230 may be manipulated by a roller pump or other pump device in order to force fluid through the inlet tubing 204 (e.g., into soaking tub 202 and/or out through outlet tubing 206).

In one embodiment, compressible segment 230 may be configured, by the material used and/or by its placement along inlet tubing 204, to be loaded into a roller pump and/or raceway (e.g., of an agitator device or controller device).

According to one example, compressible segment 230 comprises a segment of compressible silastic material approximately 9 inches in length, that may be loaded through a dual head roller pump and raceway integrated in an agitator device.

According to some embodiments, inlet tubing 204 and/or outlet tubing 206 may comprise one or more tubing guides or plugs, such as tubing guides 228 and 231, configured to ensure that the tubing is installed correctly. For example, in accordance with one or more of various embodiments discussed in this disclosure, tubing may be held in place by, connected to, and/or affixed to an agitator device, controller device, pump device, and/or other type of device or apparatus. Most tubing is uniform in nature, allowing for the possibility that it may be inadvertently loaded incorrectly (and/or unsafely) in the wrong direction. Applicants have recognized that it may be advantageous, in accordance with some embodiments described in this disclosure, to provide for one or more specifically shaped guides that only line up with their respective and correspondingly shaped indents, sockets, or receptacles, to prevent loading the tubing in the wrong direction and/or an inappropriate pathway (e.g., a round protuberance will only line up with an inlet side of a tubing raceway and a square protuberance will only line up with an outlet side of the raceway).

In one or more embodiments, a tubing guide comprises a protuberance attached to the tubing. In one example, a tubing guide may comprise a cube, rectangular prism, cylinder, sphere, or other shaped guide, and at least a portion of the tubing passes through and/or is affixed to the guide. In some embodiments, tubing guides 228 and 231 may comprise specific shapes only to be inserted into their shape specific counterparts for a desired tubing path and/or direction (e.g., as tubing pathway guides and/or raceway direction guides).

According to some embodiments, the shape of a tubing guide is configured to be removably inserted into a correspondingly shaped socket, receptacle or depression. When the tubing guide is inserted in the appropriately-shaped socket (e.g., a cylindrical or spherical guide into a round hole), the guide holds the tubing in place (e.g., in a roller pump assembly).

According to some embodiments, one or more tubing guides may be used to eliminate the possibility of inadvertently connecting or loading tubing in the wrong direction.

In one example, the proximal side of the compressible segment 230 of inlet tubing 204 may pass through or otherwise be attached to a round protuberance (e.g., ½ inch diameter), and the distal side of the compressible segment 230 may pass through or otherwise be attached to a square protuberance (e.g., ½ inch square). The round protuberance is for insertion into a first corresponding socket to ensure, for example, that the inlet tubing is oriented properly to bring fluid (e.g., from an IV bag attached to that end of the inlet tubing) into a roller pump assembly.

It will be readily understood that although two insert guides are depicted in FIG. 2, a tubing guide comprising an asymmetrical design, in combination with a corresponding receptacle design, may be sufficient for ensuring that tubing is oriented correctly (e.g., that inlet or outlet tubing is not loaded in the wrong direction), if inserting the asymmetrical guide ensures that the tubing can only be oriented in one direction. Any number and/or design of insert guides may be appropriate, as deemed desirable for a particular implementation.

In one or more embodiments, the inlet tubing 204 and outlet tubing 206 may be joined by a y-type tubing connection 222, such as a Thermo Scientific™ Nalgene® y-type polypropylene tubing connector or wye connector by Teleflex. In one embodiment, at least one end of y-type tubing connection 222 passes through male connector 220, allowing for fluid to flow in and/or out of soaking tub 202. Y-type tubing connection 222 may be useful, in accordance with some embodiments, to facilitate (1) filling the soaking tub with physiologic solution (not shown) and/or (2) emptying the soaking tub of the bloody suspension fluid (not shown).

According to some embodiments, inlet tubing 204 comprises one or more intravenous (IV) bag spikes 236 for supplying one or more types of fluid (e.g., physiologic fluid) to a cell resuspension tub system via inlet tubing 204. Applicant has recognized that, in accordance with one or more embodiments, soaking surgical laundry with physiologic suspension solution causes the dilution of the coagulation components of whole blood, making clotting of the blood in the surgical laundry and/or a cell saver less likely and yielding more salvageable blood from the collection process. According to some embodiments, a cell resuspension or reclamation process may comprise a step of soaking bloody surgical sponges in a suspension fluid to allow the surgical laundry to become saturated with suspension fluid, further liberating blood from the woven cotton fibers of the sponges. According to one or more embodiments, a clinician may add other medicines, solutions, agents, and/or infusible products (e.g., in addition to physiologic solution) to the soaking tub (e.g., at a pre-determined ratio). It may be advantageous, in accordance with some embodiments, to use one or more additional products to enhance the yield of the bloody suspension fluid from surgical laundry and/or to add one or more agents to the suspension fluid to make re-infusion of that fluid better for the patient and/or to increase the viability of recovered cells. Diluting the blood with a physiologic solution or other agent may inhibit the enzymatic reactions that are necessary for coagulation to occur. In one example, the use of blood collection agents added or mixed with the physiologic solution such as citrate-phosphate-dextrose (CPD-A1 or A2) may aide in the viability, anticoagulation, nourishment, and suspension of any sponge blood reclaimed during a soak/rinse process.

In one or more embodiments, inlet tubing 204 may comprise one or more clamps 234 (e.g., Roberts clamps) for starting, stopping, adjusting, or otherwise controlling the release of fluids (e.g., physiologic solution) into the inlet tubing 204 (e.g., from one or more IV bags).

According to some embodiments, inlet tubing 204 may comprise a y-type spike connection 232, allowing two or more IV bags (not shown) to be attached to the inlet tubing (e.g., via IV bag spikes 236).

As depicted in FIG. 2, inlet tubing 204, clamps 234, and y-type spike connection 232 may allow for multiple products to be introduced individually into a single tubing line and/or to be combined (e.g., in a predetermined ratio) into a common tubing line that may be run through one or more types of pumps, heaters, and/or sensors. In accordance with some embodiments, one or more additional tubing lines may be utilized. In one or more embodiments, multiple tubing lines may be run through one or more of any pumps, heaters, sensors, and/or other components. In some embodiment, inlet tubing 204 may be configured to include a first tubing line having its own respective one or more IV spikes and/or spike connections for introducing products into the first tubing line, and may further include a second tubing line having its own respective one or more IV spikes and/or spike connections for introducing products into the second tubing line. In some embodiments, the separate first and second tubing lines may be run through the same one or more components and/or the first tubing line may be run through one or more components that the second tubing line is not run through. In some embodiments, the first and second tubing lines may join together (e.g., via a tubing connection) after at least one of the tubing lines has been run through one or more components.

According to one hypothetical example, a first tubing line for introducing physiologic fluid and a separate, second tubing line for introducing a drug (e.g., heparin) both may be run through the same roller pump assembly (e.g., roller pump assembly 909) and then connect together into a common tubing line after passing through the roller pump assembly. The amount of fluid and/or amount of the drug being introduced may be individually controlled (and/or a desired ratio achieved) based on, for example, the respective diameter of the corresponding tubing line (e.g., 3/16-1/4 inch for the physiologic solution tubing, 1/8 inch for the drug tubing). In another example, a first and second tubing line may connect together after the first tubing line has passed through a roller pump assembly and after the second tubing line has passed separately through the same or a different roller pump assembly and also through a heater. In another example, a first and a second tubing line may connect together after both have passed separately through two or more components. In another example, a first and a second tubing line may connect together after the first tubing line has passed through at least one component and before the second tubing line passes through any component. In one embodiment, one or more separate tubing lines do not connect (e.g., each is pumped and empties separately into a soaking tub). Various configurations of one or more tubing lines, components, and/or connections, suitable for desirable implementations, will be readily understood those skilled in the art in light of this disclosure.

As discussed in this disclosure, outlet tubing 206 may be loaded through one or more of: an occlusive clamp, a flow sensor, and/or an air detector (e.g., mounted on an agitator device or controller device). In one embodiment, the outlet tubing 206 has a 3/16-inch inner diameter.

In one or more embodiments, outlet tubing 206 may comprise a portion 270 for loading through a flow sensor and/or air detector (e.g., a combined flow/air detector). According to some embodiments, outlet tubing 206 may comprise at least one type of sensor for measuring an amount of cells (e.g., red blood cells) in a fluid. In one embodiment, outlet tubing 206 may comprise a hematocrit sensor 224 (e.g., an In-Line hematocrit sensor by In-Line Diagnostics Corporation) for measuring a volume of recovered red blood cells suspended in a physiologic solution (e.g., red blood cells extracted from surgical sponges in soaking tub 202).

According to some embodiments, soaking tub 202 and/or one or more other components of cell resuspension tub system 200 may comprise one or more sterile components. For example, soaking tub 202, inlet tubing 204, and/or outlet tubing 206 may be sterilized and/or packaged in a sterile manner appropriate for medical use (e.g., for introduction to and use on a sterile field; during a surgical or other medical procedure).

According to some embodiments, soaking tub 202 and/or one or more other components of cell resuspension tub system 200 are for a single use. For example, cell resuspension tub system 200 may be used during only a single surgical procedure, for only a single patient, for extracting cells from only a single set of one or more surgical articles, and/or for only one cell resuspension process.

Figure 3:
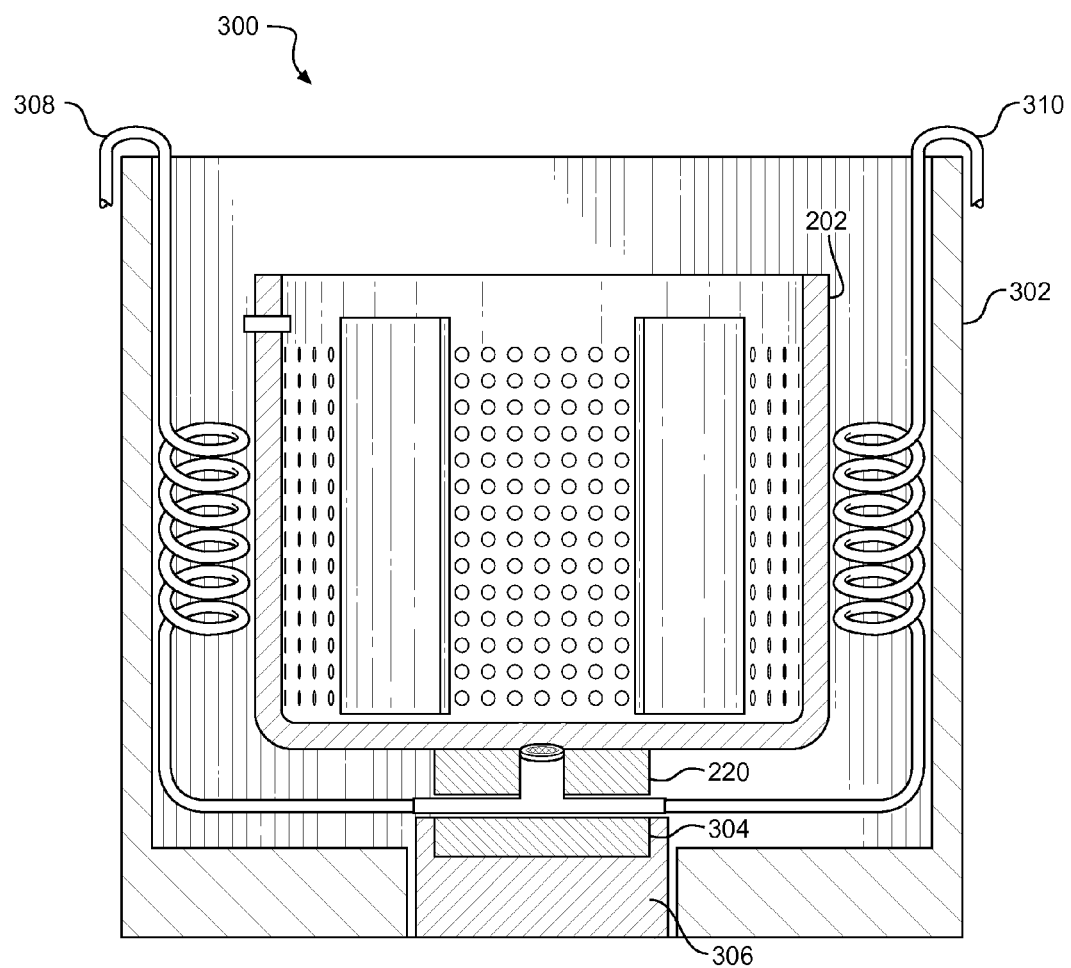
FIG. 3 is a cross-section view of a cell resuspension system according to one or more embodiments.

FIG. 3 depicts a cross-section view of an example cell resuspension system 300 according to one or more embodiments. As shown in FIG. 3, the example cell resuspension system 300 comprises a soaking tub 202 mechanically coupled with a cell resuspension agitator device 302. In particular, in accordance with some embodiments, a connector 220 of the soaking tub 202 comprises a portion 304 for removably mounting or otherwise coupling the soaking tub 202 to the connector 306 of the cell resuspension agitator device 302.

In one example, as shown in FIG. 3, the connector 306 comprises a female connector (e.g., comprising or attached to a drive mechanism for rotating soaking tub 202) configured for receiving portion 304, which is configured to fit into the connector 306.

According to some embodiments, connector 306 comprises, is coupled to, or is integrated into a motor assembly comprising a motor for rotating the soaking tub 202.

As shown in FIG. 3, the example cell resuspension system 300 may comprise fluid input means 308 (e.g., inlet tubing 204) for introducing fluid into the soaking tub 202 and/or fluid output means 310 (e.g., outlet tubing 206) for removing fluid (e.g., fluid including suspended cells) from the soaking tub 202. In one embodiment, outlet tubing 206 may be connected to a cell saver and/or a cardiopulmonary machine.

According to some embodiments, a controller device, agitator device, and/or cell resuspension tub system may comprise one or more temperature thermistors for measuring a temperature of fluid in one or more of a fluid intake system, fluid output system, and/or soaking tub.

Figure 4:
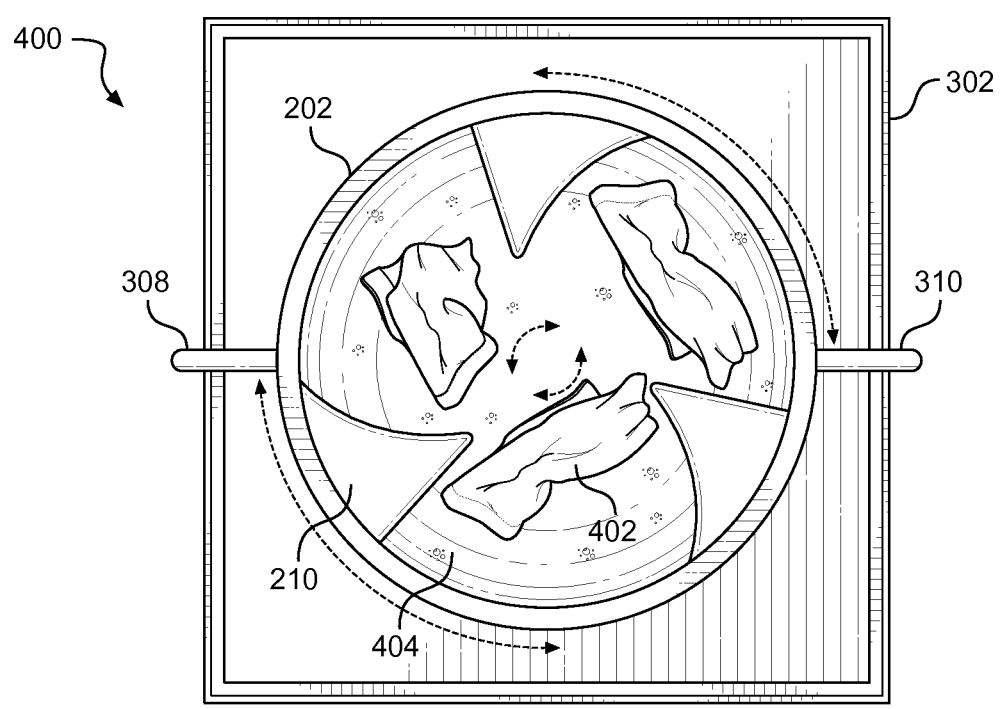
FIG. 4 is a top view of a cell resuspension system according to one or more embodiments.

FIG. 4 depicts a top view of an example cell resuspension system 400 comprising a soaking tub 202 rotatably mounted in a cell resuspension agitator device 302, in accordance with one or more embodiments. As shown in FIG. 4, the cell resuspension agitator device 302 may be configured (e.g., using a rotating drive shaft coupled to the soaking tub 202) to rotate soaking tub 202 clockwise and/or counterclockwise. In some embodiments, cell resuspension system 400 is configured to rotate soaking tub 202 clockwise and counterclockwise through a limited range of rotation (e.g., 270 degrees, 90 degrees, 2.5 rotations, 1080 degrees). According to some embodiments a length of slack tubing (e.g., configured as one or more tubing coils) in fluid input means 308 and/or fluid output means 310 may be configured to accommodate a desired range of rotation of the soaking tub 202.

As depicted in FIG. 4, soaking tub 202 may comprise one or more fins 210 for agitating the fluid 404 when the soaking tub 202 is rotated. According to some embodiments, the back and forth rotation causes the fins 210 to agitate the fluid 404 and/or the articles 402. In one example, the rotation of the soaking tub 202 by the cell resuspension agitator device 302 provides friction, turbulence, and/or mechanical action to the fluid 404 and/or articles 402 to remove cells (e.g., red blood cells) from the articles 402. According to one embodiment, any cells freed from the articles 402 may be suspended in the fluid 404 (e.g., for removal with the fluid 404 through outlet tubing 310).

Figure 5:
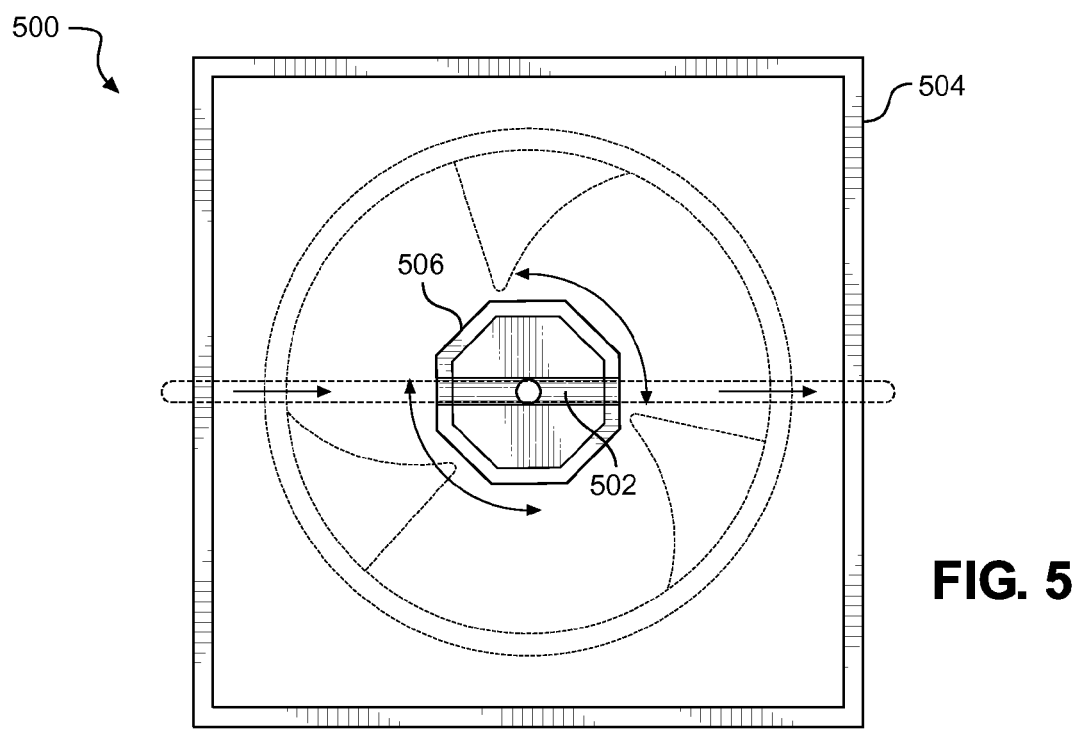
FIG. 5 is a top view of a cell resuspension agitator device according to one or more embodiments.

FIG. 5 depicts a top view of an example cell resuspension agitator device 500 according to one or more embodiments. The cell resuspension agitator device 500 may, in some embodiments, be configured for combination with a cell resuspension tub and/or cell resuspension tub system (indicated by dashed lines in FIG. 5). As shown in FIG. 5, cell resuspension agitator device 500 may comprise walled cabinet 504 (e.g., constructed of a rigid material such as, without limitation, aluminum, plastic, or stainless steel) or frame for housing, containing, and/or integrating one or more components of the agitator device. In some embodiments, embodiment cell resuspension agitator device 500 may comprise a lid and/or a bottom portion or panel (not shown). In one embodiment, cell resuspension agitator device 500 may comprise a drain for draining the agitator device should it be contaminated with spillage (e.g., from a cell resuspension tub).

As depicted in FIG. 5, cell resuspension agitator device 500 may comprise an agitating drive assembly 506 for providing rotating or other type of agitating motion to a cell resuspension tub (e.g., to produce friction and/or turbulent motion for freeing cells from surgical articles). In some embodiments, agitating drive assembly 506 may comprise or be coupled to a power source (not shown), such as a motor and/or drive shaft, for rotating a cell resuspension tub. In one embodiment, cell resuspension agitator device 500 comprises an agitating drive assembly 506 but does not comprise a cabinet, frame, or walls.

In accordance with some embodiments, as discussed in this disclosure, agitating drive assembly 506 may be or may comprise a male, female, or other type of connector for coupling with a corresponding connector of a cell resuspension tub. For example, agitating drive assembly 506 may comprise a female connector (e.g., connector 306 (FIG. 3)) for rotatably coupling with male connector 220 of cell resuspension tub 202, as shown in FIG. 2. Although shown as having a multifaceted, hexagonal shape, it will be readily understood that agitating drive assembly 506 may be configured in any shape suitable for securely and rotatably connecting with a correspondingly shaped connector of a cell resuspension tub.

In some embodiments, agitating drive assembly 506 may comprise a groove, passageway, or other type of channel 502 for allowing the tubing or other means for conducting fluid (e.g., inlet tubing 204 (FIG. 2)) to pass through one or more sides of the agitating drive assembly 506 when a soaking tub receiving such tubing (e.g., via a y-type tubing connection) is mounted in agitating drive assembly 506.

Figure 6:
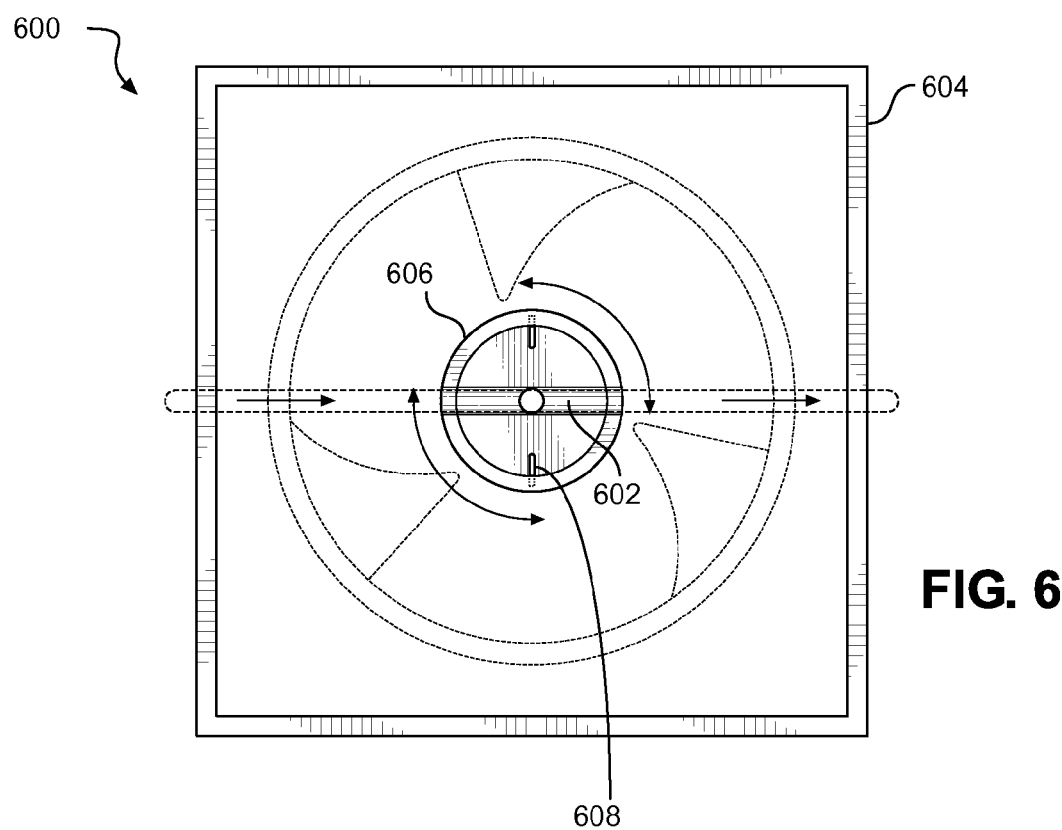
FIG. 6 is a top view of a cell resuspension agitator device according to one or more embodiments.

FIG. 6 depicts a top view of an example cell resuspension agitator device 600 according to one or more embodiments. Similar to the cell resuspension agitator device described with respect to FIG. 5, the cell resuspension agitator device 600 may, in some embodiments, be configured for combination with a cell resuspension tub and/or cell resuspension tub system (indicated by dashed lines in FIG. 6). Cell resuspension agitator device 600 may comprise an agitating drive assembly 606 for providing rotating or other type of agitating motion to a cell resuspension tub. In some embodiments, agitating drive assembly 606 may comprise or be coupled to a power source (not shown).

As shown in FIG. 6, in accordance with some embodiments, agitating drive assembly 606 comprise a male, female, or other type of connector comprising one or more fins, blades, or other rotation securing element 608 protruding from an interior side of the agitating drive assembly for coupling with a corresponding connector of a cell resuspension tub. For example, the rotation securing element(s) 608 may fit into corresponding receptacles, slots, sockets, or the like, in the cell resuspension tub when the tub is properly mounted. Accordingly, the rotation securing element 608 may help to secure the cell resuspension tub to agitating drive assembly 606 and/or provide rotational motion to the cell resuspension tub when the agitating drive assembly 606 is rotating. Although shown as having a generally circular shape, it will be readily understood that agitating drive assembly 606 may be configured in any shape, and/or with any number and/or shape of rotation securing elements 608, suitable for securely and rotatably connecting with a correspondingly shaped connector of a cell resuspension tub.

In some embodiments, agitating drive assembly 606 may comprise one or more channels 602, for allowing the tubing or other means for conducting fluid to pass into a mounted soaking tub. According to some embodiments, as shown in FIG. 6, cell resuspension agitator device 600 may also comprise a cabinet 604.

According to some embodiments, an agitating drive assembly may be configured to couple magnetically and/or electromagnetically (e.g., with a corresponding cell resuspension tub connector) in order to provide for a secure connection. In one embodiment, a magnetized female connector may be utilized to hold securely a corresponding male connector of a soaking tub, without necessarily requiring the male connector be of a multifaceted design or requiring connecting fins, blades, or the like, in order for the female connector to rotate the soaking tub.

Figure 7:
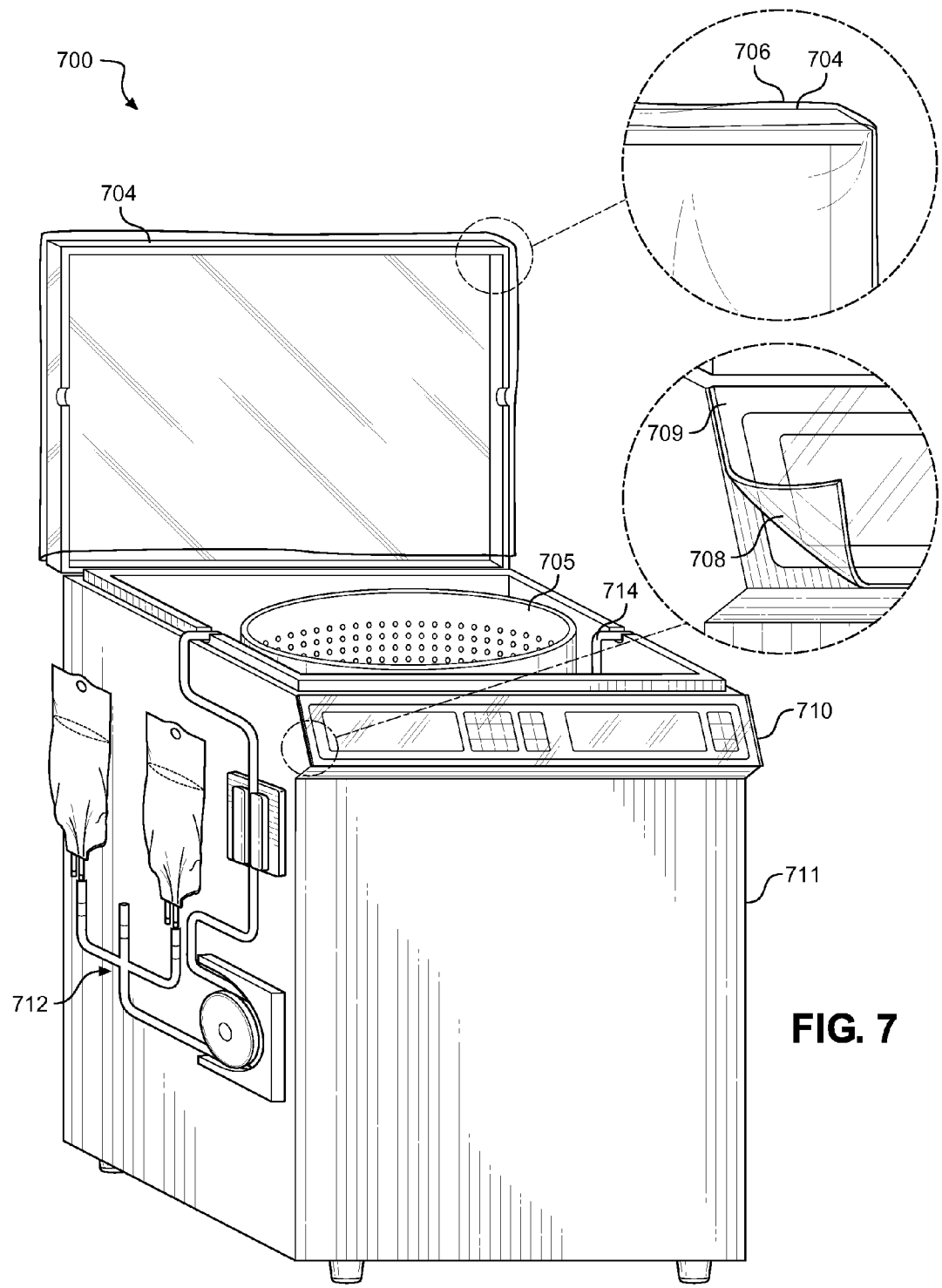
FIG. 7 is a perspective view of a cell resuspension system according to one or more embodiments.

FIG. 7 depicts a perspective view of an example cell resuspension system 700 according to one or more embodiments. Cell resuspension system 700 may comprise, in accordance with some embodiments: a lid 704, a cell resuspension tub 705, a user control panel 710, a cell resuspension controller device 711, fluid intake system 712, and fluid output system 714.

The lid 704, for example, may comprise a lid hinged to the top of a side of the cell resuspension controller device 711 (e.g., hinged to the top of the back panel). In some embodiments, the lid 704 may be constructed of plastic and/or glass. The lid 704 may be clear, in accordance with one or more embodiments, to allow a user to see into the interior of the cell resuspension controller device 711 and/or cell resuspension tub 705. As shown in FIG. 7, the lid 704 may comprise one or more notches or grooves to allow passage of tubing or other means for providing fluid in and/or out of the cell resuspension controller device 711 and/or cell resuspension tub 705.

In one embodiment, the underside of lid 704 may comprise a cover or lid configured to cover the top opening of cell resuspension tub 705 to prevent spilling or splashing fluid from the tub (e.g., during a filling, draining, and/or agitating process). In one example, a cover of a shape and size suitable for sealing or closing the opening at the top of the cell resuspension tub 705 may be affixed to or integrated with the underside of lid 704. According to various embodiments, the underside of a cover for sealing the tub opening against fluid spillage may be concave, convex, or flat. In one embodiment, a cover having an underside with a convex surface extending into the tub (e.g., coming to a downward point or a spherical surface bowing into the tub) may advantageously allow any spilled or splashed fluid accumulating on the underside of the cover to drain, in accordance with the gravitational pull, toward the center of the cover.

Alternatively, a tub system may comprise a covering for a tub that is not attached to lid 704 (or is removably attachable to lid 704).

As shown in a close-up detail in FIG. 7, in some embodiments a sleeve 706 may be used with the lid 704. For example, a sterile, single-use, plastic sleeve having an opening on at least one end, may be placed by a user around the lid 704 prior to initiating a cell resuspension process. In some embodiments, one or more protective coverings or sheets, rather than a single sleeve, may be used to cover the top and/or underside of the lid 704. In one embodiment, the sleeve 706 is transparent or clear enough to allow a user to view the interior of the cell resuspension controller device 711 and/or the cell resuspension tub 705 through the lid 704.

As shown in FIG. 7, the user control panel 710 may comprise, in some embodiments, one or more displays, touchscreens, buttons, switches, keypads, or the like, and/or any combination of desirable input and/or output devices deemed desirable for initiating, monitoring, modifying, controlling, and/or receiving information about a cell resuspension process. Various types of functions that may be provided by a cell resuspension controller device are described in this disclosure, and one or more of such functions may be provided via the user control panel 710.

As shown in a close-up detail in FIG. 7, in some embodiments a user control panel covering 708 (e.g., a sheet of plastic) may be used to protect and/or keep sterile the user control panel 710. In one embodiment, as depicted in FIG. 7, the user control panel covering 708 may be removably affixed (e.g., using an appropriate adhesive) at least at portion 709 (e.g., an adhesive strip along the top of the user control panel covering 708) to the user control panel 710. According to some embodiments, the user control panel covering 708 may be for a single use and may be replaced by a user for each use of the cell resuspension controller device 711.

The cell resuspension controller device 711 may comprise, as shown in FIG. 7, an outer cabinet with lid 704 and user control panel 710. In some embodiments, the cell resuspension controller device 711 may comprise one or more of: a processor, a computer readable memory (e.g., storing computer readable instructions for directing the processor to perform a cell resuspension process), one or more input devices, one or more output devices, a power supply, a connecting drive assembly (e.g., for coupling with and rotating the cell resuspension tub 705), a motor, and/or a communication port. Cell resuspension controller device 711 may comprise and/or be in communication with, according to some embodiments, a cell resuspension agitator device 500 for coupling with and rotating a soaking tub (e.g., soaking tub 202 of cell resuspension tub system 200).

According to some embodiments, the cell resuspension controller device may be configured (e.g., in accordance with one or more hardware and/or software controllers) to provide for one or more of the following functions:

a. monitoring and/or controlling input of physiologic fluid to a soaking tub and/or cell resuspension tub system
b. monitoring and/or controlling one or more roller pump or other types of pump devices for controlling the filling and/or emptying of a soaking tub and/or cell resuspension tub system
c. monitoring and/or controlling one or more clamping valves to facilitate the filling of a soaking tub with a physiologic solution
d. monitoring and/or controlling one or more clamping valves to facilitate the emptying of a soaking tub of physiologic solution (e.g., bloody physiologic suspension solution)
e. monitoring and/or controlling a temperature of a fluid (e.g., a physiologic solution)
f. monitoring and/or controlling one or more heat exchange surfaces (e.g., for controlling temperature)
g. controlling the motion of a multifaceted receiver to provide for turbulence and/or rotational motion in a soaking tub (e.g., rotating a fluid filled tub back and forth through a 180-240 degree range to create turbulence in the fluid)
h. spinning and/or rotating a soaking tub
i. controlling the operation of a lid and/or latch (e.g., allowing/securing access to an interior of an agitator device for installing and/or removing a soaking tub and/or cell resuspension tub system)
j. tracking, monitoring, storing (e.g., for documentation to a patient's medical record), and/or transmitting information related to one or more of:
  volume of blood loss (e.g., as collected from sponges)
  volume of physiologic solution fluid in (e.g., to a soaking tub)
  volume of (bloody) suspension fluid out (e.g., from a soaking tub)
  a hematocrit measure of the suspension fluid The cell resuspension tub 705, as discussed with respect to various embodiments in this disclosure, may comprise a soaking tub, connector for connecting the soaking tub to a cell resuspension agitator device, a filter, tubing, and/or one or more tubing connectors. For example, cell resuspension tub 705 may comprise soaking tub 202, male connector 220, filter 214, and y-type tubing connection 222. In some embodiments, cell resuspension tub 705 may be manufactured and/or sold as part of a cell resuspension tub system. For example, cell resuspension tub 705 may be provided as a sterile, single-use soaking tub with fluid intake system 712 (e.g., inlet tubing 204) and/or fluid output system 714 (e.g., outlet tubing 206), as part of a single-use cell resuspension tub system, for use with cell resuspension controller device 711.

According to some embodiments, fluid intake system 712 may comprise one or more of the following: physiologic fluid, tubing, a tubing connector, a clamp, an IV bag spike, an IV bag, a compressible tubing segment, a pump, a heat exchange element, and/or a heating element. According to one example, the fluid intake system 712 of FIG. 7 may comprise one or more of the following example components discussed with respect to the example cell resuspension tub system 200 of FIG. 2: inlet tubing 204, heat exchange element 226, tubing guides 228 and 231, compressible segment 230, IV bag spikes 236, clamps 234, and/or y-type spike connection 232.

According to some embodiments, fluid output system 714 may comprise one or more of the following: physiologic fluid, tubing, a tubing connector, a clamp, a compressible tubing segment, a pump, a heat exchange element, a heating element, a hematocrit sensor, and/or a cell saver. According to one example, the fluid output system 714 of FIG. 7 may comprise one or more of the following example components discussed with respect to the example cell resuspension tub system 200 of FIG. 2: outlet tubing 206 and/or heat exchange element 226.

Figure 8:
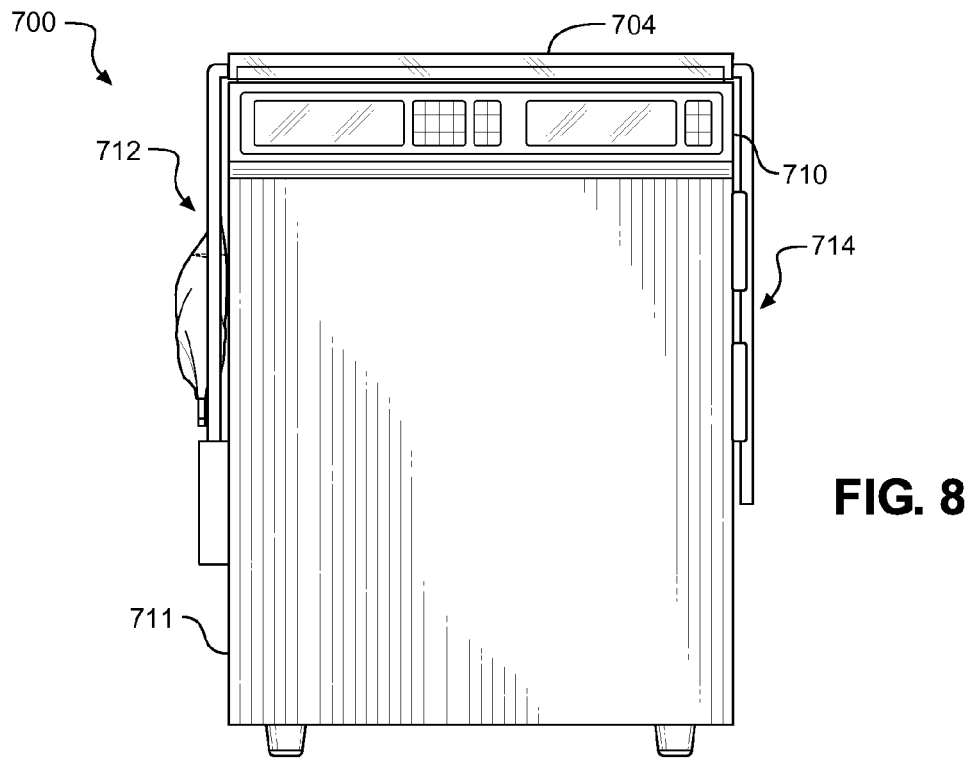
FIG. 8 is a front view of a cell resuspension system according to one or more embodiments.

FIG. 8 depicts a front view of the example cell resuspension system 700 according to one or more embodiments. As shown in FIG. 8, the example cell resuspension system 700 may comprise: cell resuspension controller device 711, including lid 704 and user control panel 710. As depicted, lid 704 may be closed, while the configuration of lid 704 (e.g., using notches or other passageways for tubing) may still allow fluid intake system 712 to provide fluid into the interior of cell resuspension controller device 711 (e.g., into a mounted soaking tub (not shown)) and may still allow fluid to exit via fluid output system 714. It will be readily understood by one skilled in the art, in light of this disclosure, that the placement of various components described in FIG. 8 may vary from what is depicted (e.g., the user control panel may be on an upper side of the cell resuspension controller device 711 and/or integrated into lid 704).

Figure 9:
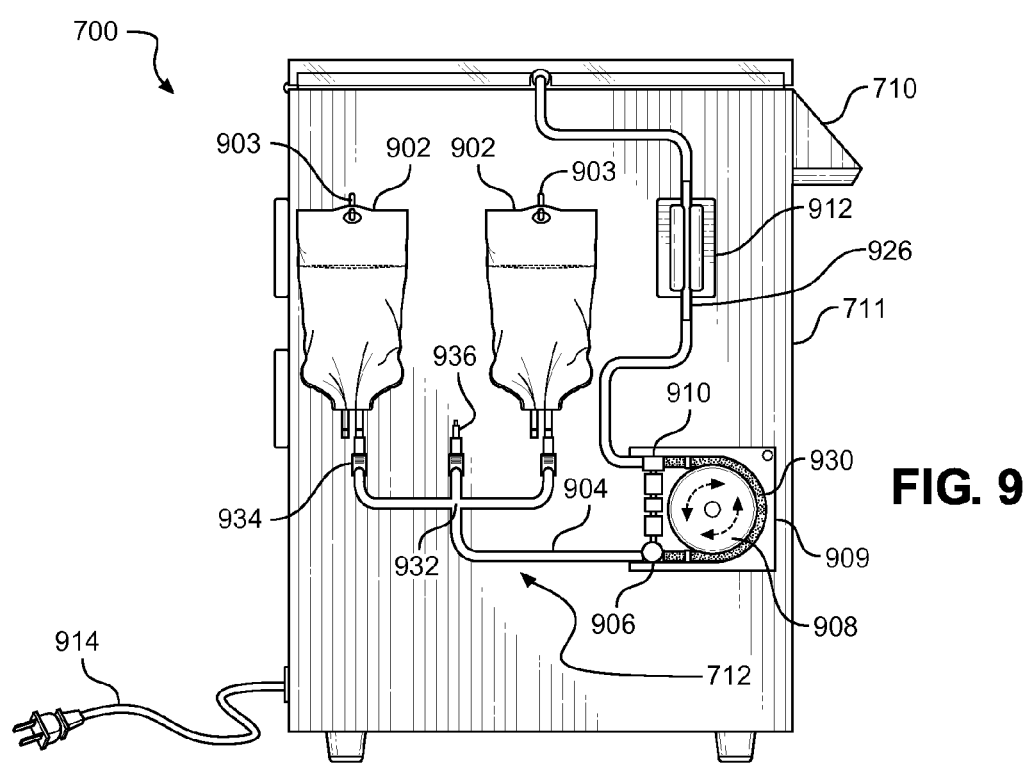
FIG. 9 is a side view of a cell resuspension system according to one or more embodiments.

FIG. 9 depicts an example side view of the example cell resuspension system 700 according to one or more embodiments. In particular, FIG. 9 depicts example components of an example fluid intake system for providing fluid to the cell resuspension system (e.g., into a soaking tub (not shown)) for use in resuspending cells that were collected in surgical articles (e.g., bloody surgical sponges). According to some embodiments, fluid intake components may comprise one or more of the following: IV bags 902, IV bag hooks 903 (e.g., for holding IV bags 902), IV bag spikes 936 (e.g., for receiving fluid from IV bags 902), clamps 934 (e.g., for controlling flow of fluid from IV bags 902), y-type spike connection 932, tubing 904 (e.g., PVC tubing), roller pump assembly 909 and roller pump 908, tubing guides 906 and/or 910 (e.g., for ensuring that the tubing is loaded in the correct direction into the roller pump assembly 909), compressible segment 930, heat exchange segment 926, and/or heating element 912.

Various types of pumps, including roller pumps and/or various positive displacement pumps, suitable for conducting fluid through tubing are known to those skilled in the art. As depicted in FIG. 9, according to some embodiments, at least a portion of tubing 904 may be loaded into a roller pump assembly 909 for pumping fluid (e.g., from IV bag 902) into, for example, a soaking tub (not shown) of the cell resuspension system 700. In one example, a compressible segment 930 of tubing may be loaded into a channel or "raceway" (e.g., a metallic raceway) of the roller pump assembly 909 and around the roller pump 908. In one example, the roller pump 908 comprises an occlusive, dual headed roller pump having two heads in opposition to one another. When the roller pump assembly 909 is activated (e.g., via the user control panel 710), the roller pump 908 rotates, acting on the compressible segment 930 and forcing fluid away from a fluid source (e.g., IV bag 902). Alternatively or in addition, one or more other pumps (e.g., roller pumps) may be used to advance fluid into and/or out of a cell resuspension tub or tub system. According to some embodiments, a controller device and/or sensor may determine an amount of fluid added to a cell resuspension tub and/or system (e.g., from IV bags) based on a determination of an amount of fluid passing through the raceway. In one example, the amount of fluid passing through the raceway (e.g., per stroke of the raceway) may be determined based on an inner diameter of the tubing.

In one embodiment, the roller pump assembly 909 may be provided with or attached to tubing 904, and may be configured to plug into a socket or other receptacle by which it may be powered and/or controlled by cell resuspension controller device 711. In another embodiment, the roller pump assembly 909 may have a power source and/or controller not provided by cell resuspension controller device 711. For example, the tubing 904 may be coupled to a stand-alone pump device (e.g., with its own controls and/or user control interface).

As shown in FIG. 9, an example fluid intake system 712 of the example cell resuspension system 700 may also comprise one or more tubing guides 906 and/or 910. Each of the tubing guides 906 and 910 may fit into a respective, correspondingly shaped socket (e.g., of the roller pump assembly 909) such that a user is required to load the tubing 904 in the correct direction through the roller pump assembly 909.

Applicant has recognized that the temperature and viability of any blood may decrease significantly over time once it is outside the body and/or if allowed to equilibrate with the environmental temperature (e.g. of an operating room). As the temperature of red blood cells decreases, so does the ability of the red blood cells to transfer oxygen. Accordingly, in some embodiments, a cell resuspension system may provide for heating and/or maintaining a desired temperature of resuspended cells, which may improve the viability of red blood cells and their ability to transfer oxygen, thereby improving the quality of the recovered blood for purposes of autotransfusion, if desired.

The example cell resuspension system 700, according to some embodiments, may comprise one or more heating elements 912 and/or one or more heat exchange elements 926, to heat fluid in a fluid intake system, soaking tub, and/or fluid output system. In one example, heating element 912 may comprise a heater such as an electric conductive heat exchanger. In one embodiment, as depicted in FIG. 9, heat exchange element 926 may be a portion of tubing 904 configured to fit into a corresponding channel in (or otherwise be coupled with) heating element 912. In one embodiment, the heating element 912 may be provided with or attached to tubing 904, and may be configured to plug into a socket or other receptacle by which it may be powered and/or controlled by cell resuspension controller device 711. In another embodiment, the heating element 912 may have a power source and/or controller not provided by cell resuspension controller device 711. For example, the tubing 904 may be coupled to a stand-alone heating element (e.g., with its own user interface for setting desired temperature). Although depicted in FIG. 9 as part of a fluid intake path, alternatively or in addition, one or more heating elements may be used in accordance with some embodiments to heat fluid in a cell resuspension tub and/or traveling through a fluid output system. In one embodiment, a heating element may be embodied in a cell resuspension tub. For example, a heating element (e.g., electric wires) may be placed between the inner and the outer walls of a soaking tub for warming the suspension fluid. In one embodiment, such wiring may travel (e.g., along with wiring for the fill sensor or other electrical components) and exit the tub (e.g., at the bottom connector).

The example cell resuspension system 700, according to some embodiments, may further comprise the user control panel 710 and/or power connection 914 (e.g., a power cord) for providing electrical power to one or more components of the cell resuspension system 700. According to one embodiment, the cell resuspension system 700 may comprise an electrical power source (e.g., a battery, a generator).

As discussed with respect to one or more embodiments in this disclosure, a cell resuspension system may provide for collecting cells (e.g., red blood cells) from surgical articles (e.g., surgical sponges) using fluid and a rotating soaking tub. After a desired period of time and/or after a desired amount of cells have been recovered, the fluid, now including the suspended cells, may be removed from the soaking tub via a fluid output system. In some embodiments, a pump (e.g., a roller pump) may be used to draw or force the fluid out of the soaking tub. In some embodiments, a fluid output system may conduct the collected cells, in the fluid, to a cell saver and/or may comprise a cell saver or other device for removing cells borne by the fluid.

Although FIG. 9 depicts an example fluid intake system configured to introduce one or more products (e.g., fluids, agents) through various components using a single, common line of tubing, it will be readily understood (as discussed with respect to FIG. 2) that two or more separate tubing lines (e.g., each with a respective one or more IV bag spikes) may be utilized and/or may connect to one another in various ways, as deemed desirable for a particular implementation.

Figure 10:
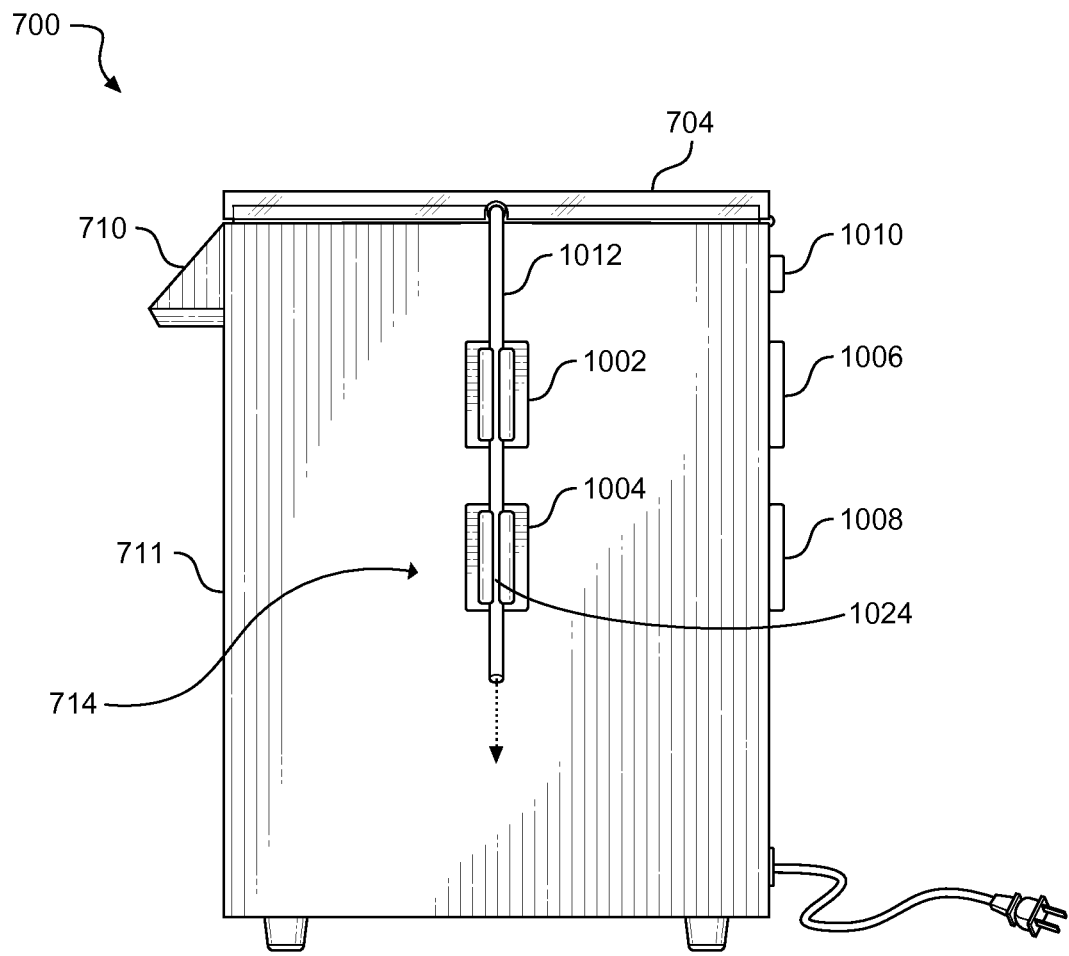
FIG. 10 is a side view of a cell resuspension system according to one or more embodiments.

FIG. 10 depicts another example side view of the example cell resuspension system 700 according to one or more embodiments. As shown in FIG. 10, the cell resuspension system 700 may comprise the cell resuspension controller device 711 (including the lid 704 and user control panel 710) and a fluid output system 714. According to some embodiments, the fluid output system 714 may comprise one or more of: tubing 1012 (e.g. PVC tubing), a flow/air detector 1002, and/or a hematocrit sensor 1004. As indicated by the directional arrow, fluid passes out of the cell resuspension controller device via tubing 1012. In one embodiment, the fluid may pass through a flow/air detector 1002, such as a flow/air detector by Transonic Corporation, providing for both a volume measurement of fluid over a period of time as well as for the presence/detection of air.

In some embodiments, the fluid may pass through a hematocrit sensor 1004 for measuring an amount of red blood cells or other cells suspended in the fluid. In one embodiment, the tubing 1012 may comprise a hematocrit sensor component 1024 for coupling with the hematocrit sensor 1004. For example, a section of tubing 1012 may contain a sensor "window" for installing into a hematocrit sensor (e.g., integrated in an agitator device cabinet), allowing the hematocrit sensor to transmit light energy into the tubing for use in analyzing the fluid. In some embodiments, based on the amount of light that is reflected the hematocrit sensor 1004 and/or a controller device may calculate a value and a saturation of hemoglobin in the fluid.

In one embodiment, the hematocrit sensor 1002 and/or flow/air detector 1002 may be in communication with a processor of the cell resuspension controller device 711, such as for transmitting measurements taken of the fluid to the processor (e.g., for display via user control panel 710 and/or other user interface). Some embodiments may comprise storing and/or transmitting an indication of information determined using one or more sensors described in this disclosure (e.g., a controller device may transmit the information to a data storage device via a communications network).

As shown in FIG. 10, the cell resuspension system 700, according to some embodiments, may also comprise at least one bar code scanner 1010 (e.g., a USB barcode scanner by Unitech), network interface 1006 (e.g., for receiving and/or transmitting patient case information, fluid information, and/or cell information), and/or equipotential binding posts 1008 to facilitate ensuring the electrical safety of a controller device and/or agitator device (e.g., when in use around flammable anesthetics and gases like oxygen). In some embodiments, network interface 1006 may comprise a wireless communications adapter and/or a wired network port for communicating with one or more computers via a communications network (e.g., the Internet, a hospital's intranet).

As shown in FIG. 9 and in FIG. 10, various fluid intake and/or fluid output components may be mounted onto and/or removably attached to, or integrated with, an apparatus or device (e.g., the cell resuspension controller device 711). For example, IV bags may be hung on the side of a controller device, tubing removably loaded into a roller pump that is integrated with a controller device, a heat exchange element of inlet tubing may be removably secured in a heating element integrated with a controller device, and/or a portion of outlet tubing may be coupled with a flow/air detector and/or a hematocrit sensor affixed to a controller device. It will be readily understood, however, that any one or more of the fluid system components described in this disclosure does not have to be physically attached to a side or other portion of the cell resuspension controller device. For example, one or more of the pump, IV bags, tubing (e.g., other the portion of tubing that enters the cell resuspension controller device and/or soaking tub), sensors, and/or heating element may be free standing, configured with or as a separate apparatus or device, or otherwise not affixed to a side of a cell resuspension controller device or cell resuspension agitator device.

Figure 11:
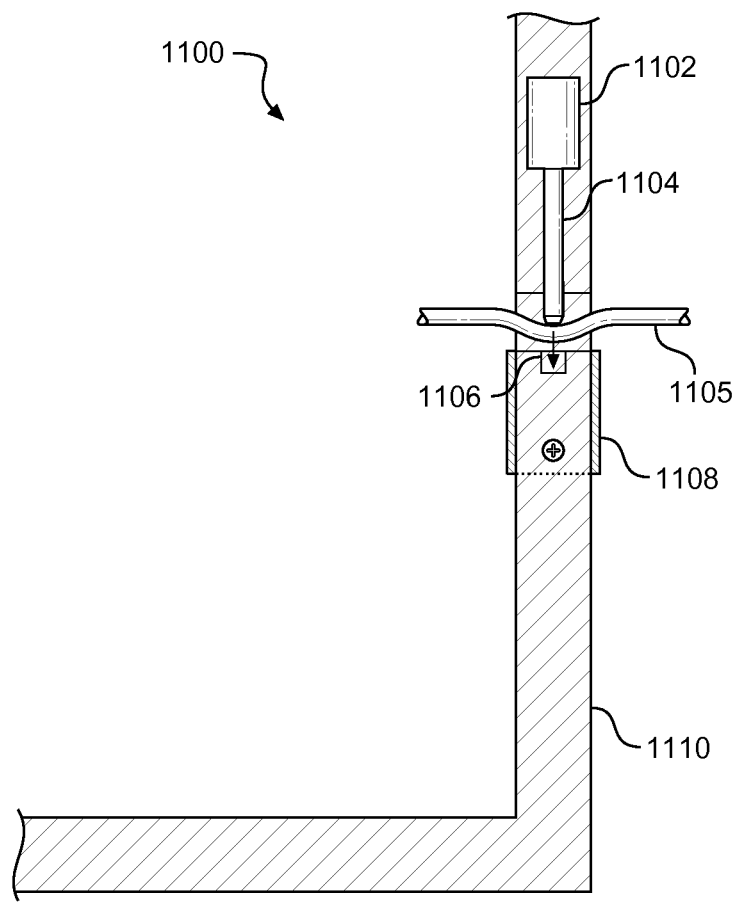
FIG. 11 is a top view of an occlusion clamp assembly according to one or more embodiments.

FIG. 11 depicts a top view of an example occlusion clamp assembly 1100 according to one or more embodiments. Occlusion clamp assembly 1100 may be useful, in accordance with some embodiments, for clamping fluid tubing (e.g., of fluid intake system 712 and/or fluid output system 714). In one or more embodiments, the occlusion clamp assembly 1100 comprises occlusion motor 1102 for driving and withdrawing occlusion stem 1104. Occlusion motor 1102 is configured to (i) drive occlusion stem 1104 (e.g., upon receiving a signal from a controller device) into tubing 1105 and into stem receiver 1106 to clamp tubing 1105 and stop the flow of fluid (and/or other materials) through the tubing 1105; and (ii) withdraw occlusion stem 104 from tubing 1105 to allow for the flow of fluid through the tubing 1105. In some embodiments, occlusion clamp assembly 1100 may comprise a striker plate assembly 1108 against which the drive occlusion stem 1104 compresses the tubing 1105.

As depicted in FIG. 11, the example occlusion clamp assembly 1100 may be mounted, for example, on a side, panel, or frame 1110 of a cell resuspension system (e.g., an exterior cabinet panel of a cell resuspension agitator device or cell resuspension controller device), to allow for controlling the flow of fluid passing via tubing into and/or out of the device.

Figure 12:
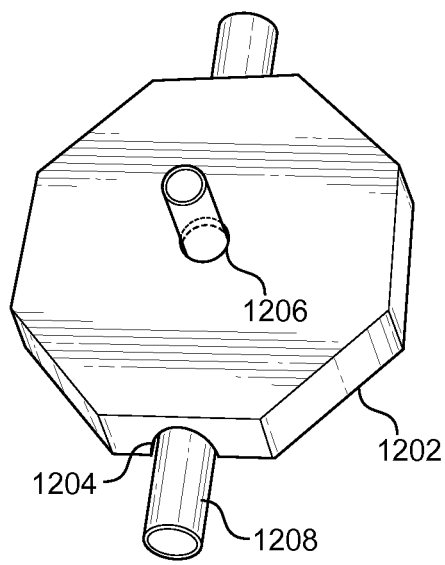
FIG. 12 is a perspective view of an example connector of a cell resuspension tub system, according to one or more embodiments.
Figure 13:
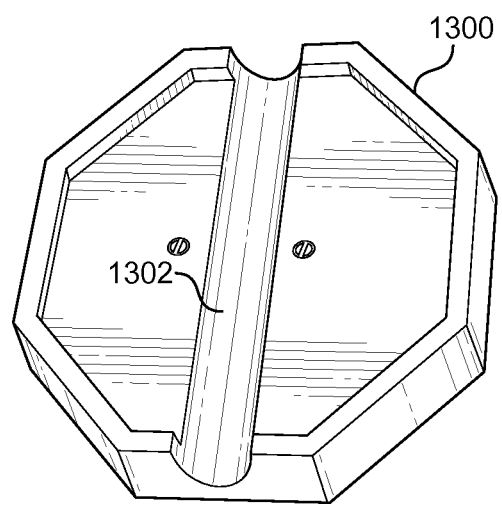
FIG. 13 is a perspective view of an example connector of an agitator device, according to one or more embodiments.
Figure 14:
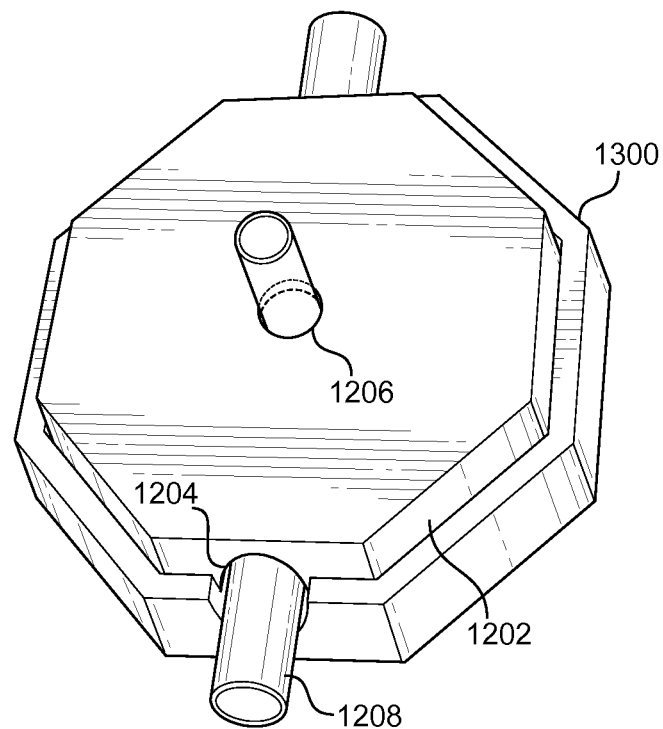
FIG. 14 is a perspective view of an example connector of a cell resuspension tub system coupled with an example connector of an agitator device, according to one or more embodiments.

FIG. 12 and FIG. 13 depict perspective views of an example connector 1202 and an example connector 1300, respectively, of a cell resuspension system, according to one or more embodiments. In some embodiments, the connector 1202 may be connected to and/or integrated with a cell resuspension tub (not shown) of a cell resuspension tub system and may be configured for coupling the cell resuspension tub to a cell resuspension agitator device (not shown) via connector 1300. As depicted in FIG. 12, connector 1202 may comprise a male connector configured of a shape appropriate for inserting into a correspondingly shaped female connector of an agitator device (or vice versa). As shown in FIG. 12, the connector 1202 may comprise a tubing passageway 1206. In one embodiment, the tubing passageway 1206 may allow for tubing to pass through the connector 1202 and into a soaking tub (e.g., soaking tub 202). As shown in FIG. 12, the connector 1202 also may comprise a tubing passageway or channel 1204. Similarly, the connector 1300 may comprise a tubing passageway or channel 1302. In one or more embodiments, as depicted in FIG. 14, the tubing channel 1204 and tubing channel 1302 may allow for tubing 1208 (e.g., y-type tubing connection 222) to pass into the connector 1202 (from one or both sides) and/or through the tubing passageway 1206 while the connector 1202 is coupled with corresponding connector 1300 of FIG. 13. Accordingly, fluid may be allowed to pass into and/or out of a soaking tub while the tub is coupled via connector 1202 to connector 1300 of a drive shaft assembly (e.g., of a motor or other type of agitator device) for rotating the soaking tub.

Figure 15:
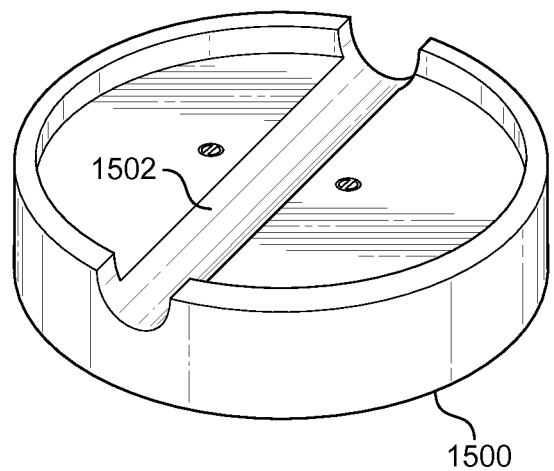
FIG. 15 is a perspective view of an example connector of an agitator device, according to one or more embodiments, for connecting to a cell resuspension tub system.

FIG. 15 is a perspective view of an alternative example connector 1500 of an agitator device, according to one or more embodiments, for connecting to a cell resuspension tub system. Similar to the example connector 1300 (FIG. 13), example connector 1500 may comprise a tubing channel 1502 for receiving a holding tubing securely when the connector 1500 is coupled with a soaking tub. Although the example connector 1500 is circular in shape, it will be readily understood in light of this disclosure that connectors may be configured in any of various shapes and/or sizes suitable for a desired implementation.

Figure 16:
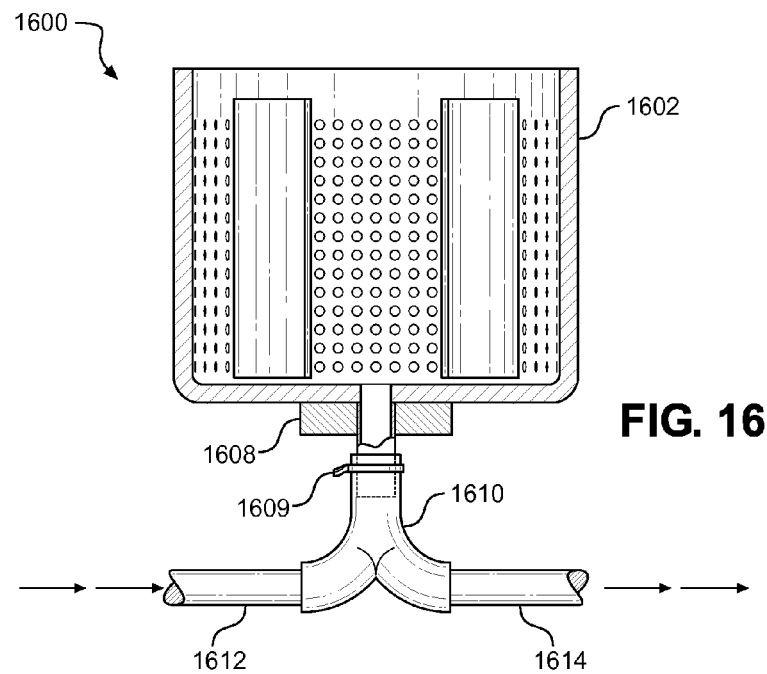
FIG. 16 is a cross-section view of a cell resuspension tub system according to one or more embodiments.

FIG. 16 depicts a cross-section view of an example cell resuspension tub system 1600 according to one or more embodiments. Cell resuspension tub system 1600 comprises a soaking tub 1602 and a rotating connector 1608 for connecting the soaking tub 202 to a means for rotating the soaking tub 1602 (e.g., a drive shaft assembly connected to a motor). The example cell resuspension tub system 1600 comprises a clamp 1609 for preventing leaks (e.g., a tie band cable clamp) and a y-type tubing connection 1610 for connecting the soaking tub 1602, inlet tubing 1612, and outlet tubing 1614. In contrast to some other embodiments discussed in this disclosure, the y-type tubing connection 1610 is not secured to the rotating connector 1608, allowing the soaking tub 1602 and the y-type tubing connection 1610 to move independently of one another. For example, if the rotating connector 1608 is rotatably secured to a rotating motor (e.g., not shown), the y-type tubing connection 1610 may remain relatively still or unaffected even while the soaking tub 1602 is rotating or spinning.

Figure 17:
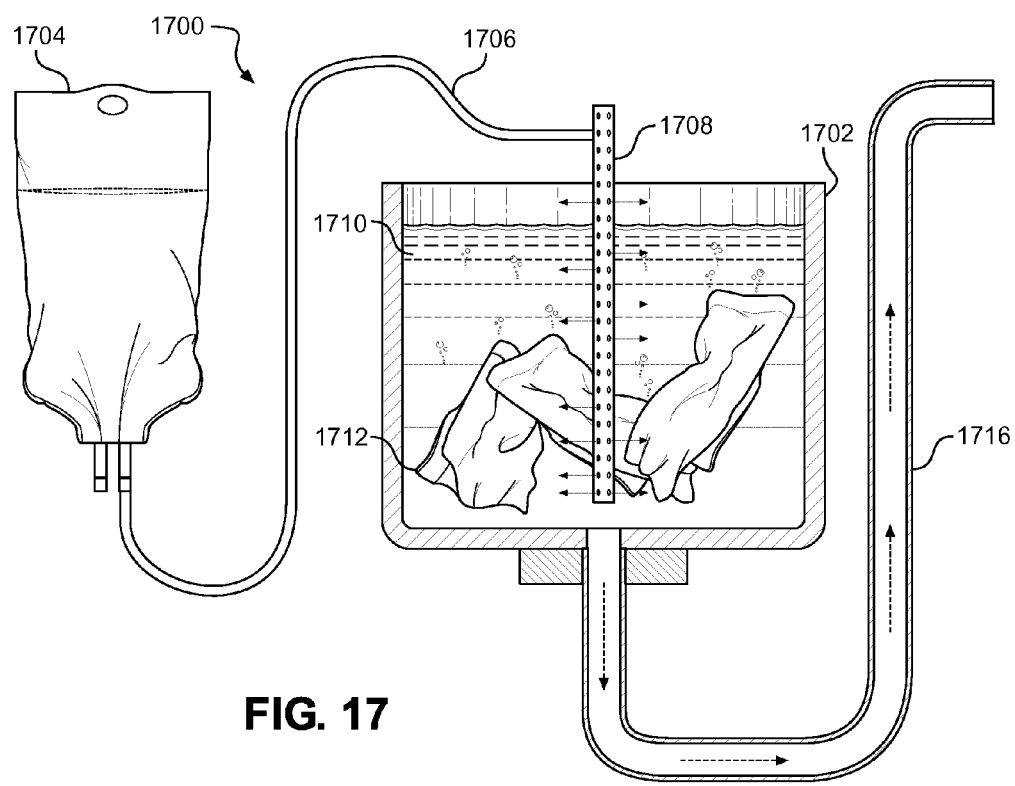
FIG. 17 is a cross-section view of a cell resuspension tub system according to one or more embodiments.

FIG. 17 depicts a cross-section view of an example cell resuspension tub system 1700 according to one or more embodiments. Cell resuspension tub system 1700 comprises a soaking tub 1702 for reclaiming cells from articles 1712 in fluid 1710. In contrast to some other embodiments discussed in this disclosure, cell resuspension tub system 1700 includes a fluid intake system 1706 for providing fluid 1710 (e.g., via PVC tubing from IV bag 1704) to soaking tub 1702 via the opening at the top of soaking tub 1702. In one example, fluid intake system 1706 may comprise tubing and/or a fluid dispensing element 1708 for releasing fluid into the soaking tub 1702. As shown in FIG. 17, the fluid dispensing element 1708 may comprise one or more holes through which fluid 1710 may enter from the tubing into the soaking tub 202. Also in contrast to some other embodiments discussed in this disclosure, cell resuspension tub system 1700 does not require fluid to be both input and output in the same manner. For example, as shown in FIG. 17, a fluid output system 1716 may draw fluid (e.g., bearing recovered cells) via tubing through the bottom of the soaking tub 1702 (e.g., and to a cell saver device).

Alternatively, or in addition, in some embodiments, fluid may be input to the soaking tub via another opening in the soaking tub (other than a top opening) and/or fluid may be added to the soaking tub through one opening (e.g., through the bottom of soaking tub 1702), while fluid containing any covered cells is extracted (e.g., using a suction pump device) through another opening of the soaking tub (e.g., via tubing out of the top opening).

D. Example Systems and Devices

The following describes an example integrated cell resuspension appliance, referred to as the "Agitator," configured to provide for one or more of various functions described in this disclosure, in accordance with one or more embodiments. None of the examples, configurations, and/or features described with respect to the Agitator are to be understood as necessarily limiting any embodiment of the present invention. Various other embodiments and examples are described in this disclosure, and others will be readily understood by those skilled in the art in light of the descriptions in this disclosure.

According to the example implementation, the Agitator may be configured as a mechanical device for receiving and moving a sterile, disposable and/or single-use soaking tub (and its associated tubing). In one variation, the Agitator is 26 inches square by 32 inches tall, with an opening at the top, and rests upon a stand with a plurality of wheels. The example Agitator device has a clear plastic lid on a hinge, allowing the lid to be open or closed depending on the cycle that is being utilized (e.g., Open, Start, Fill, Spin, Agitate, or Drain). The Agitator may be vented (e.g., sharing the same atmospheric pressure as the surrounding environment), or not, as deemed desirable for a particular implementation.

The example Agitator device comprises multiple control buttons and a display screen for displaying data, on the front of the Agitator. Case data collection (e.g., collection of information related to a type of procedure, length of procedure, surgeon, patient identifier that uniquely identifies a patient) and transmission may be accomplished via either a wireless card or a wired network port (e.g., located on the rear of the device).

The example Agitator device comprises a female, multi-faceted connector that receives and locks the underside of a disposable soaking tub, for rotating or otherwise agitating the soaking tub. The left side of the Agitator, for example, comprises a 4-inch diameter, occlusive, dual headed roller pump with its heads at 180 degrees in opposition to each other. The roller pump assembly may sit, by way of example, inside of a metallic raceway. On one side of the metallic raceway is a shaped indentation or socket; on the opposite side of the raceway is a differently shaped indentation or socket.

The example Agitator device also may comprise an electrically heated, metallic heat exchange surface (e.g., on an inflow tubing channel), made of a resistive coil under a metal surface designed to heat physiologic fluid via the principle of conduction.

According to the example embodiment, the Agitator device comprises a temperature thermistor and one or more buttons on a front surface allowing for user interface and control. On the right side of the example Agitator are a combination flow sensor and air detector for use on the outflow tubing via a tubing channel (e.g., not more than 1 inch recessed into the device), a powered automatic occlusion clamp (e.g., controlled by the Agitator), and a hematocrit sensor. The Agitator device is powered by AC current and may or may not include a battery backup.

According to one embodiment, a cell resuspension tub system may be embodied as a tubing kit comprising: a sterile soaking tub and tubing set, one or both of which may be individually wrapped; a sterile plastic lid cover or sleeve; a sterile plastic panel cover (e.g., self-adhesive for affixing to a user control panel); a sterile accessory drain line; and/or one or more other items (e.g., sensors, pumps, heaters, etc.).

E. Processes

According to one example process in accordance with some embodiments, one or more users (e.g., nurses or other medical professionals in an operating room) and/or one or more controller devices may perform one or more of the following: setting up a cell resuspension system for use; reclaiming cells from surgical laundry via the cell resuspension system; and/or processing resuspended cells for autotransfusion (e.g., via a cell saver system). According to some embodiments, a process for reclaiming cells from surgical laundry via a cell resuspension system may comprise one or more of: initiating and/or terminating a fluid filling process; initiating and/or terminating an agitation process; initiating and/or terminating a fluid removal process; and/or disposing of one or more components of a used cell resuspension tub system.

Figure 18:
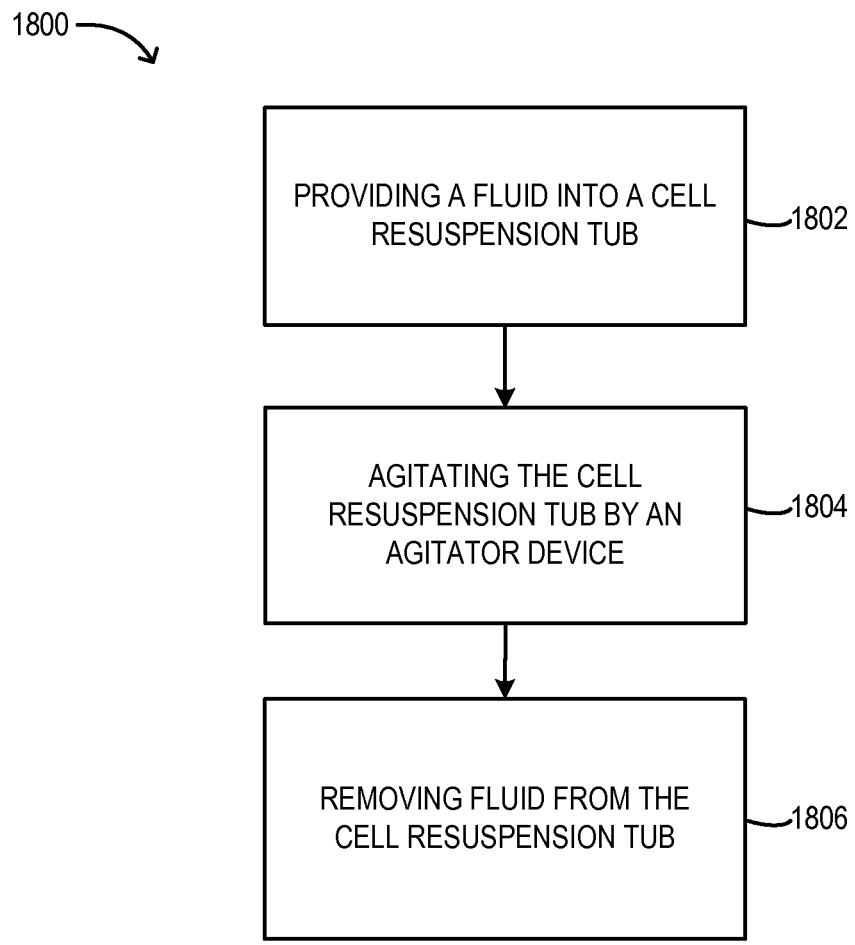
FIG. 18 is a flowchart of a method according to one or more embodiments.

According to some embodiments, setting up a cell resuspension system for use may comprise one or more users performing one or more of the following:

powering on the agitator device opening a lid of the agitator device (e.g., manually, or using an "Open" button of a user control panel)

passing a (sterile) soaking tub onto the surgical field covering the lid with a sterile plastic lid cover inserting or otherwise connecting the soaking tub with the agitator device (e.g., by inserting the soaking tub into a female connector at the bottom of the agitator device)

removing or otherwise disconnecting a soaking tub (e.g., a previously used tub) from the agitator device placing inlet tubing in the appropriate location for loading the inlet tubing (e.g., off the corresponding side of the agitator device)

placing outlet tubing in the appropriate location for loading the outlet tubing closing the lid (e.g., to maintain sterility of the soaking tub and the inside of the agitator device)

loading the inlet tubing into a heat exchange element loading the inlet tubing into a roller pump assembly loading the outlet tubing through one or more of an occlusion clamp, a flow sensor, and an air detector removing one or more sterile caps from the ends of the tubing set attaching an IV bag spike into an IV bag of physiologic fluid opening one or more tubing clamps (e.g., Roberts clamps)

connecting a sterile accessory drain line from the outlet tubing to a cell saver machine attaching a sterile, self-adhesive plastic cover to a user control panel of the agitator device Referring now to FIG. 18, a flow diagram of a method 1800, according to one or more embodiments is shown. The method 1800 will be described herein as being performed by an integrated controller/agitator device. It should be noted, however, that in some embodiments one or more of the steps of method 1800 may be performed by a controller device, while one or more other steps may be performed by another type of device (e.g., a controller device, a pump, a heater) and/or by a human user. Further any steps described herein as being performed by a particular type device may, in some embodiments, be performed by a human.

According to some embodiments, the method 1800 may comprise providing a fluid (e.g., physiologic suspension solution) into a cell resuspension tub, at 1802. In one embodiment, providing the fluid may be performed manually by a user and/or in response to an instruction from a user or actuation of a corresponding user control by a user (e.g., via a user control panel or interface). In some embodiments, providing the fluid may be initiated and/or performed automatically in response to a signal or other communication from a controller device (e.g., in response to executing software instructions, in response to receiving a fill instruction from a user). As discussed with respect to various embodiments in this disclosure, providing the fluid may comprise initiating an automated fill process for transmitting fluid from a fluid source (e.g., an IV bag) via a tubing system, and/or starting and controlling a pump device to fill a cell resuspension tub. As described in this disclosure, the fluid may comprise a physiologic suspension solution that may include one or more agents.

The method 1800 may comprise, in some embodiments, agitating the cell resuspension tub (e.g., automatically) by an agitator device, at 1804. For example, as discussed with respect to various embodiments in this disclosure, agitating a cell resuspension tub (e.g., including fluid and surgical laundry inserted by a user or otherwise received by a cell resuspension system) may comprise operating a motor to rotate or otherwise agitate a cell resuspension tub removably coupled to the motor. In one embodiment, a controller device may transmit a signal to start a rotating motor. In some embodiments, agitating the cell resuspension tub may comprise agitating fluid and/or and at least one item of surgical laundry (e.g., bloody surgical sponges) in the cell resuspension tub.

The method 1800 may comprise, according to some embodiments, removing fluid from the cell resuspension tub, at 1806. In some embodiments, removing fluid may comprise removing at least a portion of the fluid provided to the cell resuspension tub (at 1802) along with any cells released from surgical laundry and resuspended in the fluid. In one or more embodiments, the removed fluid may comprise physiologic suspension solution, resuspended cells, and/or at least one drug or other agent. Various embodiments for draining or otherwise removing fluid and recovered cells from a tub are described in this disclosure.

According to some embodiments, the method 1800 may further comprise one or more of: transmitting the removed fluid to at least one of a cell saver and an autotransfusion device, and maintaining a desired temperature of fluid (e.g., within a predetermined temperature range) using a thermometer and/or heater. Maintaining a desired temperature may include heating and/or monitoring fluid before it enters the cell resuspension tub, while it is in the tub, and/or after it is removed from the tub. In one example, fluid is maintained at approximately a normothermic temperature for the type of cells being recovered (e.g., the normothermic temperature of 98.6 F for human blood).

According to an illustrative and non-limiting example of a method of use of a cell resuspension system comprising an example integrated controller/agitator device and tub system or kit (comprising a soaking tub and corresponding tubing set), the example agitator device and soaking tub are designed to work in concert with each other. The agitator device is a reusable device and the soaking tub (with its corresponding tubing set) is a disposable, single-use device. The agitator device is designed, according to the non-limiting example, to be set up and operated in a sterile operating room environment by operating room personnel (e.g., a "scrub" nurse and/or a "circulating" nurse). Although described with respect to a single nurse, it will be readily understood that respective steps may be performed by any number of users. According to the example method, when the agitator device is to be used, the individually wrapped and sterile disposable soaking tub and tubing set are passed onto the sterile field to the "scrubbed" OR personnel for setup. The agitator device preferably is positioned next to the surgical field and plugged into AC current by the circulating nurse. A nurse, for example, may cover the lid with supplied sterile plastic lid cover, and also insert the soaking tub into a multifaceted female receiver at the bottom of the agitator device. The nurse may also place the inlet side of the tubing off the appropriate side of the agitator device, place the outlet tubing off the appropriate side of the agitator device, and close the lid, as the inside of the device is now setup and sterile. A nurse may load the inlet tubing into a heat exchange surface of the agitator device and into a roller pump assembly, and load the outlet tubing through the occlusion clamp, flow sensor, air detector, and hematocrit sensor of the agitator device. The sterile cap on the end of the tubing set may be left on the tubing until the system is ready for use.

Continuing with the illustrative example method of use, a nurse attaches IV bag spikes of the inlet tubing into a physiologic fluid IV bag and opens the tubing clamps (e.g., Roberts clamps). The nurse also attaches the sterile accessory drain line to an operating room cell saver machine and attaches a sterile self-adhesive plastic button cover to an operator panel of the agitator device. Before, after, or contemporaneously with the insertion (e.g., by a nurse) of at least one bloody surgical sponge into the soaking tub, a nurse presses a "Fill" button of the agitator device that fills the soaking tub with an amount of physiologic solution (e.g., an amount approximately ⅔ of the total tub capacity, approximately 360 mls of fluid). If desired, additional soak volume may be added to the soaking but by depressing and holding the fill button again.

Continuing with the illustrative example method of use, a user presses a "Start" button of the agitator device, causing the lid to lock, the multifaceted receiver to attach to the underside of the soaking tub, and a drain clamp of the agitator device to occlude the tubing set. The multifaceted receiver engages the tub and begins the agitation of the sponges. This agitation may continue for a period of time sufficient to liberate the blood from the sponge. The period of time may be predetermined and the agitation may be terminate automatically by the agitator device. Alternatively, or in addition, the agitation process may be terminated at any time manually by a user pressing a "Stop" button (e.g., of a user control panel). For instance, this may allow an operator to place more bloody sponges in the agitator device (e.g., as they are collected). Pressing a "Start" button again after a stop resumes a previously started cycle where it was terminated.

Continuing with the illustrative example method of use, after the process of agitating the soaking tub (e.g., after the completion of a preprogrammed cycle and/or upon actuation of a "Finish" button by a user), the agitator device may automatically sound an alert (e.g., "cycle complete" alert) and/or open the closed occlusion clamp to allow the bloody suspension fluid to drain from the vessel. In one example, the fluid is exposed to suction created by a cell saver or other device, in order to drain the tub. Once an air detector detects air in the outlet tubing, the occlusion clamp again engages and occludes the outlet tubing. In one example, the device may automatically (and/or at the initiation of a user) "dry spin" the tub (e.g., for a three minute cycle) at a speed designed to further remove blood from the sponges through centrifugal motion. Once the air detector again (or still) detects air in the outlet tubing, indicating the tub is empty, the agitator device may cause the occlusion clamp to again engage and occlude the outlet tubing. The operator may press an "Option" button to open the lid and may remove the processed sponges. Once the processed sponges are out of the soaking tub, the operator may again initiate a fill function (e.g., by pressing a "Fill" button) to fill the soaking tub with physiologic solution, in preparation for more blood soaked surgical sponges. If no additional sponges need to be washed (e.g., a surgical operation has been completed), the operator may "unload" the soaking tub and tubing set (e.g., by disconnecting it from the agitator device). A nurse may dispose of the soaking tub and/or the tubing set(s) (e.g., in an appropriate biohazard container).

According to the illustrative example method, the integrated controller/agitator device may display case information via a display screen of the device. For example, the device may display one or more of: a volume of physiologic solution used, a volume of bloody suspension fluid out, a temperature of the fluid, a number of cycles processed, and/or an average hematocrit value of the suspension fluid.

F. Example Interfaces and Applications

One or more of the methods described in this disclosure may involve one or more interface(s). One or more methods may include, in some embodiments, providing an interface through which a user may (i) submit, request, and/or receive information about a patient and/or cells (reclaimed and/or to be reclaimed) and/or (ii) initiate one or more steps of a cell resuspension process.

In one hypothetical example, a program being executed by a processor (e.g., embodied in a cell resuspension controller device) initiates a process via a user interface to reclaim blood cells from bloody surgical laundry. Information about different blood reclamation options may be received from a user via the user interface, and various types of information about the processing, fluid involved in the resuspension process, and/or recovered blood cells may be displayed and/or otherwise output to the user via the user interface.

Figure 19:
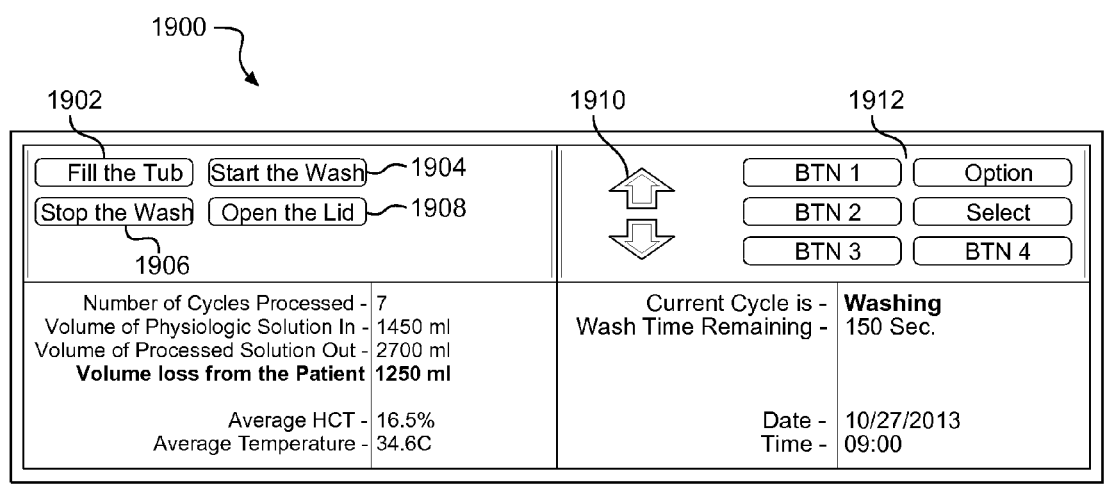
FIG. 19 is a diagram of an example user interface according to one or more embodiments.

FIG. 19 illustrates an example interface 1900, according to one or more embodiments, by which a user (e.g., a medical professional operating a cell resuspension controller device of a cell resuspension system) may initiate various phases of a cell resuspension process to extract cells (e.g., red blood cells) from surgical sponges, instruments, organs, human and/or animal tissue, and/or other types of surgical articles.

Example elements of interface 1900 include a button 1902 to initiate a process of filling a soaking tub, a button 1904 to initiate a washing process to collect cells from surgical articles, a button 1906 to stop the washing process, and a button 1908 to release and/or open a lid (e.g., lid 704 of example cell resuspension system 700). For example, pressing any of the buttons 1902, 1904, 1906, and/or 1908 may cause a controller device (e.g., cell resuspension controller device 711) to perform the corresponding function (e.g., in accordance with corresponding computer readable software instructions executable by a processor of the controller device).

Interface 1900 may further comprise one or more input controls 1910 for increasing, decreasing, inputting, modifying, and/or selecting values, settings, and/or options by a user. In one example, input controls 1910 may be configured as arrow buttons for moving between options and/or fields on the user interface. Although only two arrows are depicted in FIG. 19, it will be readily understood that any number of arrows (e.g., left and right arrows) and/or types of input controls (e.g., buttons, pointer devices, keyboards, touchpads, arrow keys, etc.) may be used as deemed desirable for a particular implementation. In some embodiments, any one or more of buttons 1912 may be configured to allow a user to assign one or more functions to the button(s).

In one embodiment, a user may have the ability to enter data using the interface 1900 (e.g., via corresponding form fields), such as, without limitation, case data, patient name, name(s) of a surgeon and/or other medical personnel, an identifier that identifies a type of surgery, a type of drug (e.g., a drug or other agent added to a solution being added to a soaking tub), a concentration of drug, and an amount of drug used). In some embodiments, one or more types of information may be retrieved (e.g., by a controller device) from one or more remote data servers.

In some embodiments, various types of information may be presented to a user via interface 1900. For example, as shown in FIG. 19, information transmitted to a user via interface 1900 may comprise, without limitation, one or more of the following:
- information related to a number of cell resuspension cycles processed and/or scheduled
- information related to a volume or other measure of fluid input to a cell resuspension system (e.g., 1450 ml)
- information related to a volume or other measure of fluid recovered and/or processed by a cell resuspension system (e.g., 2700 ml)
- information related to a volume or other measure of cells (e.g., blood cells) lost from a patient (e.g., 1250 ml)
- information related to a temperature of fluid being input to and/or processed by a cell resuspension system (e.g., an average temperature)
- information related to a measure of resuspended cells per volume of fluid (e.g., an average hematocrit (HCT) percentage level)
- information related to a previous, current, and/or future status or phase of a cell resuspension process (e.g., "Washing", "Complete", "Lid open", "Tub filling")
- information related to how long a previous, current, and/or future status or phase of a cell resuspension process has taken or will take (e.g., "Wash time remaining—150 seconds")
- current date and/or time information
- information related to a patient (e.g., a patient whose blood is being resuspended)

According to one embodiment, the volume salvaged from the contents of a surgical sponge or other article may be calculated as a difference between a volume of physiologic fluid in and a volume of physiologic solution out. For example: 2700 ml (volume of bloody suspension solution out)−1450 ml (volume of physiologic solution in)=1250 ml (volume of reclaimed volume). In some cases, items such as surgical laundry may be contaminated with irrigation fluid or other types of fluids, and not solely blood. Accordingly, in some embodiments, it may or may not be possible to determine whether the additional volume removed from a cell resuspension tub includes not just blood or other types of recovered cells, but also one or more fluids that were collected by the surgical laundry and released during the cell resuspension process.

Although certain types of information are illustrated in the example interface 1900, those skilled in the art will understand that the interface 1900 may be modified in order to provide for additional types of information (e.g., other patient information) and/or to remove some of the illustrated types of information, as deemed desirable for a particular implementation.

Although interface 1900 is illustrated as a single interface, those skilled in the art will readily understand, in light of the present disclosure, that the features and information of the example interface, or a subset of such features and information, may be included in more than one interface, control panel, screen display, or application window.

Additional Embodiments

According to some embodiments, systems, methods, and apparatus may be provided for the autotransfusion of recovered blood, such as blood reclaimed from surgical laundry and resuspended in a fluid in accordance with various embodiments described in this disclosure. Autotransfusion will be readily understood by those skilled in the art as a process by which a patient's own shed blood can be returned to that patient. Autotransfusion typically uses a system to acquire, process, and re-infuse shed blood volume by means of a suction style of collection. Some of the benefits of autotransfusion include a reduction in the patient's immune reactivity related to the administration of allogeneic blood (a.k.a. bank blood), an elimination of the potential for an ABO incompatibility, an elimination of the risk of transmission of blood borne diseases like Hepatitis, HIV/AIDS, Cytomegalovirus Virus (CMV), Crutchfield Jakobs Disease (CJD) among many others known or unknown. Autotransfusion also decreases the demand on the supply of blood available for transfusions. According to some embodiments, a cell resuspension system may comprise and/or may transmit resuspended blood to one or more autologous cell salvage devices or cell savers for processing and/or eventual re-infusion in a patient.

According to one or more embodiments, a device is provided for use in resuspending blood that is suspended in surgical laundry, wherein the device uses a physiologic solution to fill a vessel to extract blood. In some embodiments, the device comprises a vessel and the device is configured to fill the vessel (e.g., via a filling mechanism) with a sterile physiologic suspension solution. In one or more embodiments, the device may comprise a mechanism for controlling the filling of the vessel with a physiologic suspension solution and/or for controlling the emptying of the vessel. In one embodiment, the vessel is configured so that bloody surgical laundry may be placed (e.g., by a user) in the vessel to soak in sterile physiologic suspension solution. In one embodiment, the vessel of the example device is engaged in a mechanism for agitating the vessel to liberate blood from surgical laundry. In one embodiment, the device may include a drain line at the bottom of the vessel (e.g., to drain the blood saturated suspension fluid from the vessel).

According to some embodiments, neither agitating a cell resuspension tub, fluid, and/or surgical articles, nor releasing or resuspending cells from surgical articles, comprises the use of suction, a vacuum, or other type of negative pressure.

According to some embodiments, providing fluid to a soaking tub or other type of cell resuspension tub may not involve a pump or like device. For example, fluid may be introduced manually (e.g., by a user) into a soaking tub.

Although numerous embodiments are described in this disclosure with respect to surgical laundry, sponges, and other types of surgical articles, it will be readily understood, in light of the present disclosure, that various embodiments described in this disclosure may be configured for use with any of various types of objects an item of clothing, paper, and/or a piece of glass) that may have collected or retained cells to be recovered.

In one embodiment, a heater configured to heat physiologic suspension solution or other type of fluid used in resuspending cells may be configured for heating the fluid directly or indirectly, such as by heating tubing, IV bags, and/or a cell resuspension tub.

Interpretation

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention may be practiced with various modifications and alterations, such as structural, logical, software, and/or electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features that must be present in all embodiments.

Neither the Title (set forth at the beginning of the first page of this disclosure) nor the Abstract (set forth at the end of this disclosure) is to be taken as limiting in any way the scope of the disclosed invention(s).

Throughout the description and unless otherwise specified, the following terms may include and/or encompass the example meanings provided below. These terms and illustrative example meanings are provided to clarify the language selected to describe embodiments both in the specification and in the appended claims, and accordingly, are not intended to be limiting.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term "process" or a like term. Accordingly, any reference in a claim to a "step" or "steps" of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

As used in this disclosure, a "user" may generally refer to any individual and/or entity that operates a user device.

Some embodiments may be associated with a "user device" or a "network device". As used in this disclosure, the terms "user device" and "network device" may be used interchangeably and may generally refer to any device that can communicate via a network. Examples of user or network devices include a personal computer (PC), a workstation, a server, a printer, a scanner, a facsimile machine, a copier, a personal digital assistant (PDA), a storage device (e.g., a disk drive), a hub, a router, a switch, and a modem, a video game console, or a wireless phone. User and network devices may comprise one or more communication or network components.

As used in this disclosure, the terms "information" and "data" may be used interchangeably and may refer to any data, text, voice, video, image, message, bit, packet, pulse, tone, waveform, and/or other type or configuration of signal and/or information. Information may comprise information packets transmitted, for example, in accordance with the Internet Protocol Version 6 (IPv6) standard as defined by "Internet Protocol Version 6 (IPv6) Specification" RFC 1883, published by the Internet Engineering Task Force (IETF), Network Working Group, S. Deering et al. (December 1995). Information may, according to some embodiments, be compressed, encoded, encrypted, and/or otherwise packaged or manipulated in accordance with any method that is or becomes known or practicable.

In addition, some embodiments described in this disclosure are associated with an "indication". The term "indication" may be used to refer to any indicia and/or other information indicative of or associated with a subject, item, entity, and/or other object and/or idea. As used in this disclosure, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

"Determining" something may be performed in a variety of manners and therefore the term "determining" (and like terms) includes calculating, computing, deriving, looking up (e.g., in a table, database or data structure), ascertaining, recognizing, and the like.

A "processor" means any one or more microprocessors, Central Processing Unit (CPU) devices, computing devices, microcontrollers, digital signal processors, or like devices. Examples of processors include, without limitation, INTEL's PENTIUM, AMD's ATHLON, or APPLE's A6 processor.

When a single device or article is described in this disclosure, more than one device or article (whether or not they cooperate) may alternatively be used in place of the single device or article that is described. Accordingly, the functionality that is described as being possessed by a device may alternatively be possessed by more than one device or article (whether or not they cooperate). Where more than one device or article is described in this disclosure (whether or not they cooperate), a single device or article may alternatively be used in place of the more than one device or article that is described. For example, a plurality of computer-based devices may be substituted with a single computer-based device. Accordingly, functionality that is described as being possessed by more than one device or article may alternatively be possessed by a single device or article. The functionality and/or the features of a single device that is described may be alternatively embodied by one or more other devices that are described but are not explicitly described as having such functionality and/or features. Thus, other embodiments need not include the described device itself, but rather can include the one or more other devices that would, in those other embodiments, have such functionality/features.

A description of an embodiment with several components or features does not imply that any particular one of such components and/or features is required. On the contrary, a variety of optional components are described to illustrate the wide variety of possible embodiments of the present invention(s). Unless otherwise specified explicitly, no component and/or feature is essential or required.

Further, although process steps, algorithms or the like may be described or depicted in a sequential order, such processes may be configured to work in one or more different orders. In other words, any sequence or order of steps that may be explicitly described or depicted does not necessarily indicate a requirement that the steps be performed in that order. The steps of processes described in this disclosure may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications, does not imply that the illustrated process or any of its steps is necessary to the invention, and does not imply that the illustrated process is preferred.

It will be readily apparent that the various methods and algorithms described in this disclosure may be implemented by, e.g., appropriately- and/or specially-programmed general purpose computers and/or computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer-readable media) in a number of manners. In some embodiments, hard-wired circuitry or custom hardware may be used in place of, or in combination with, software instructions for implementation of the processes of various embodiments. Thus, embodiments are not limited to any specific combination of hardware and software.

Accordingly, a description of a process likewise describes at least one apparatus for performing the process, and likewise describes at least one computer-readable medium and/or computer-readable memory for performing the process. The apparatus that performs a described process may include components and/or devices (e.g., a processor, input and output devices) appropriate to perform the process. A computer-readable medium may store program elements and/or instructions appropriate to perform a described method.

The term "computer-readable medium" refers to any medium that participates in providing data (e.g., instructions or other information) that may be read by a computer, a processor, or a like device. Various forms of computer-readable media may be involved in carrying data, including sequences of instructions, to a processor. For example, sequences of instruction (i) may be delivered from RAM to a processor, (ii) may be carried over a wireless transmission medium, and/or (iii) may be formatted according to any one or more of various known formats, standards, or protocols (some examples of which are described in this disclosure with respect to communication networks).

Computer-readable media may take many forms, including but not limited to, non-volatile media, volatile media, and transmission media. Non-volatile media may include, for example, optical or magnetic disks and other types of persistent memory. Volatile media may include, for example, DRAM, which typically constitutes the main memory for a computing device. Transmission media may include, for example, coaxial cables, copper wire, and fiber optics, including the wires that comprise a system bus coupled to the processor. Transmission media may include or convey acoustic waves, light waves, and electromagnetic emissions, such as those generated during RF and IR data communications. Common forms of computer-readable media include, for example, a floppy disk, a flexible disk, a hard disk, magnetic tape, any other magnetic medium, a CD-ROM, DVD, any other optical medium, a punch card, paper tape, any other physical medium with patterns of holes, a RAM, a PROM, an EPROM, a FLASH-EEPROM, a Universal Serial Bus (USB) memory stick or thumb drive, a dongle, any other memory chip or cartridge, a carrier wave, or any other medium from which a computer can read.

The term "computer-readable memory" may generally refer to a subset and/or class of non-transitory computer-readable medium that does not include intangible or transitory signals, waves, waveforms, carrier waves, electromagnetic emissions, or the like. Computer-readable memory may typically include physical, non-transitory media upon which data (e.g., instructions or other information) are stored, such as optical or magnetic disks and other persistent memory, DRAM, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, USB devices, any other memory chip or cartridge, and the like.

Where databases are described, it will be understood by one of ordinary skill in the art that (i) alternative database structures to those described may be readily employed, and (ii) other memory structures besides databases may be readily employed. Any illustrations or descriptions of any sample databases presented in this disclosure are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries may be different from those described in this disclosure. Further, despite any depiction of the databases as tables, other formats (including relational databases, object-based models, hierarchical electronic file structures, and/or distributed databases) could be used to store and/or manipulate the described data. Likewise, object methods or behaviors of a database may be used to implement one or more of various processes, such as those described in this disclosure. In addition, the databases may, in a known manner, be stored locally and/or remotely from a device that accesses data in such a database. Furthermore, while unified databases may be contemplated, it is also possible that the databases may be distributed and/or duplicated amongst a variety of devices.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

What is claimed is:

1. A method comprising:
providing a physiologic suspension solution into a cell resuspension tub through a first connector connected to a bottom portion of the cell resuspension tub, the first connector having a passageway configured for allowing the physiologic suspension solution to pass through the first connector;
agitating, automatically via an agitator device comprising a second connector, the cell resuspension tub while the second connector is removably coupled to the first connector,
the cell resuspension tub including the physiologic suspension solution and at least one surgical article,
the at least one surgical article retaining cells to be resuspended; and
removing, from the cell resuspension tub through the first connector while the first connector is removably coupled to the second connector, a solution including at least a portion of the physiologic suspension solution and resuspended cells released from the at least one surgical article,
wherein the first connector connected to the bottom portion of the cell resuspension tub is connected to tubing, the tubing comprising at least one of:
inlet tubing configured for receiving the physiologic suspension solution into the cell resuspension tub through the first connector,
outlet tubing configured for removing the solution including at least a portion of the physiologic suspension solution and resuspended cells from the cell resuspension tub through the first connector, and
a y-type tubing connection configured for receiving the physiologic suspension solution into the cell resuspension tub through the first connector, and configured for removing the solution including at least a portion of the physiologic suspension solution and resuspended cells from the soaking tub through the first connector,
wherein the agitator device comprises:
a motor;
a heater; and
a controller device configured to:
control operation of a fluid input system connected to the cell resuspension tub and configured to control the providing of the physiologic suspension solution into the cell resuspension tub,
control the heater to heat the physiologic suspension solution,
control operation of the motor to agitate the cell resuspension tub, and
control operation of a fluid output system connected to the cell resuspension tub and configured to control the removing of the solution from the cell resuspension tub.

2. The method of claim 1, further comprising:
transmitting the removed solution to at least one of: a cell salvage device and an autotransfusion device.

3. The method of claim 1, wherein agitating the cell resuspension tub comprises rotating the cell resuspension tub back and forth.

4. The method of claim 1, wherein the first connector comprises a passageway configured for allowing the solution to pass through the first connector while the first connector is removably coupled to the second connector.

5. The method of claim 4,
wherein the tubing comprises the outlet tubing; and
wherein removing the solution from the cell resuspension tub through the first connector while the first connector is removably coupled to the second connector comprises:
removing the solution via the outlet tubing.

6. The method of claim 4,
wherein the tubing comprises the inlet tubing; and
wherein providing the physiologic suspension solution into the cell resuspension tub through the first connector connected to a bottom portion of the cell resuspension tub comprises:
providing the physiologic suspension solution via the inlet tubing.

7. The method of claim 1,
wherein the cell resuspension tub is a sterile, disposable cell resuspension tub.

8. The method of claim 1, further comprising:
removably coupling the first connector to the second connector by inserting the cell resuspension tub into the agitator device.

9. The method of claim 1, wherein the second connector is configured to couple with the first connector magnetically.

10. The method of claim 1, wherein the cell resuspension tub comprises a first wall and second wall inside the first wall,
the second wall including at least one fenestration for allowing fluid to pass through the second wall from the interior of the soaking tub.

11. The method of claim 1, wherein the cell resuspension tub comprises at least one fin connected to an interior surface of the cell resuspension tub, the at least one fin protruding inward from the interior surface toward the interior of the cell resuspension tub.

12. The method of claim 1, wherein the cell resuspension tub comprises a filter configured to filter the solution as it is removed from the cell resuspension tub.

13. The method of claim 1, further comprising:
transmitting at least one of cell resuspension information and patient information using a communications subsystem.

14. The method of claim 1, further comprising:
applying, using the heater, heat to at least one of: the cell resuspension tub and the physiologic suspension solution.

15. The method of claim 1, wherein the agitator device comprises at least one of the following:
a hematocrit sensor configured to measure a hematocrit value for the physiologic suspension solution removed from the cell resuspension tub,
a flow sensor configured to measure a volume of the solution removed from the cell resuspension tub, and
an air detector configured to detect air in the solution removed from the cell resuspension tub.

16. The method of claim 1, further comprising:
receiving a signal from at least one of a flow sensor and an air detector, the signal indicating an absence of fluid; and
terminating the removing of the solution from the cell resuspension tub response to receiving the signal.

17. The method of claim 1,
wherein the fluid input system comprises at least one pump device configured for the providing of the physiologic suspension solution into the cell resuspension tub.

18. The method of claim 1, further comprising:
transmitting the removed solution through a filter.

19. The method of claim 1, further comprising:
receiving a signal from a fill sensor configured to detect fluid in the cell resuspension tub, the signal indicating detection of physiologic suspension solution in the cell resuspension tub.

20. The method of claim 1, further comprising:
controlling access to an interior of at least one of the following:
the agitator device, and
the cell resuspension tub.

21. A method comprising:
providing a physiologic suspension solution into a cell resuspension tub through a first connector connected to a bottom portion of the cell resuspension tub;
agitating, automatically via an agitator device comprising a second connector, the cell resuspension tub while the second connector is removably coupled to the first connector,
the cell resuspension tub including the physiologic suspension solution and at least one surgical article,
the at least one surgical article retaining cells to be resuspended; and
removing, from the cell resuspension tub through the first connector while the first connector is removably coupled to the second connector, a solution including at least a portion of the physiologic suspension solution and resuspended cells released from the at least one surgical article,
further comprising:
coupling the first connector of the cell resuspension tub to the second connector of the agitator device,
wherein prior to coupling, the agitator device is non-sterile and the cell resuspension tub is sterile.

22. A method comprising:
providing a physiologic suspension solution into a cell resuspension tub through a first connector connected to a bottom portion of the cell resuspension tub;
agitating, automatically via an agitator device comprising a second connector, the cell resuspension tub while the second connector is removably coupled to the first connector,
the cell resuspension tub including the physiologic suspension solution and at least one surgical article,
the at least one surgical article retaining cells to be resuspended; and
removing, from the cell resuspension tub through the first connector while the first connector is removably coupled to the second connector, a solution including at least a portion of the physiologic suspension solution and resuspended cells released from the at least one surgical article,
further comprising:
removably coupling the cell resuspension tub to the agitator device.

* * * * *